(12) United States Patent
Kaneoka et al.

(10) Patent No.: US 7,777,183 B2
(45) Date of Patent: Aug. 17, 2010

(54) CHARGE PARTICLE BEAM SYSTEM, SAMPLE PROCESSING METHOD, AND SEMICONDUCTOR INSPECTION SYSTEM

(75) Inventors: Noriyuki Kaneoka, Hitachinaka (JP); Kaoru Umemura, Tokyo (JP); Koji Ishiguro, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 256 days.

(21) Appl. No.: 11/834,220

(22) Filed: Aug. 6, 2007

(65) Prior Publication Data

US 2008/0029699 A1 Feb. 7, 2008

(30) Foreign Application Priority Data

Aug. 8, 2006 (JP) ............................. 2006-216069

(51) Int. Cl.
*G01N 23/225* (2006.01)
(52) U.S. Cl. ...................... 250/306; 250/307; 250/309; 250/310; 250/311
(58) Field of Classification Search ................. 250/306, 250/307, 309, 310, 311, 492.1, 492.2, 492.21, 250/492.3
See application file for complete search history.

(56) References Cited

U.S. PATENT DOCUMENTS

| 5,517,027 | A | * | 5/1996 | Nakagawa et al. ............. 850/1 |
| 5,583,344 | A | * | 12/1996 | Mizumura et al. ..... 250/492.21 |
| 5,923,020 | A | | 7/1999 | Kurokawa et al. |
| 5,939,719 | A | * | 8/1999 | Park et al. ...................... 850/1 |
| 5,986,264 | A | | 11/1999 | Gruenewald |
| 6,373,070 | B1 | * | 4/2002 | Rasmussen ............ 250/492.21 |
| 6,583,426 | B1 | | 6/2003 | Kawanami et al. |
| 2002/0170497 | A1 | * | 11/2002 | Smirnov et al. .......... 118/723 E |
| 2002/0190207 | A1 | * | 12/2002 | Levy et al. ................... 250/306 |
| 2003/0006372 | A1 | * | 1/2003 | Morita et al. ............... 250/310 |
| 2003/0179370 | A1 | * | 9/2003 | Goldberg et al. ......... 356/237.2 |
| 2004/0178811 | A1 | * | 9/2004 | Ishitani et al. .............. 324/751 |
| 2004/0185586 | A1 | | 9/2004 | Yasutake |
| 2004/0256555 | A1 | | 12/2004 | Shichi et al. |
| 2005/0054029 | A1 | * | 3/2005 | Tomimatsu et al. ......... 435/40.5 |
| 2005/0092922 | A1 | * | 5/2005 | Muto et al. ................. 250/309 |
| 2005/0168729 | A1 | | 8/2005 | Jung et al. |
| 2005/0199828 | A1 | | 9/2005 | Tokuda et al. |
| 2005/0269511 | A1 | * | 12/2005 | Tomimatsu et al. ......... 250/310 |

(Continued)

FOREIGN PATENT DOCUMENTS

JP 8-327554 A 12/1996

(Continued)

*Primary Examiner*—Robert Kim
*Assistant Examiner*—Michael Maskell
(74) *Attorney, Agent, or Firm*—Crowell & Moring LLP

(57) ABSTRACT

A charged particle beam system, a sample processing method, and a semiconductor inspection system enable an accurate detection of a particle in a film without causing LMIS contamination and allow observation with an electron microscope quickly. A particle 65 causing a defect in a film 66 that has been detected with a separate optical inspection system is detected with an optical microscope 43 based on position information acquired by the separate optical inspection system. A sample 31 is processed with a nonmetal ion beam 22 so as to allow observation of the particle 65 with an electron microscope image or an ion microscope image, or ultimate analysis of the particle 65 with an EDX.

16 Claims, 17 Drawing Sheets

U.S. PATENT DOCUMENTS

| | | | |
|---|---|---|---|
| 2005/0278134 A1* | 12/2005 | Langer et al. | 702/118 |
| 2007/0158560 A1 | 7/2007 | Kaneoka et al. | 250/309 |
| 2007/0273945 A1* | 11/2007 | Furman et al. | 359/107 |
| 2008/0290275 A1* | 11/2008 | Kamiya et al. | 250/311 |
| 2008/0296516 A1* | 12/2008 | Tomimatsu et al. | 250/492.21 |

FOREIGN PATENT DOCUMENTS

| | | |
|---|---|---|
| JP | 10-223168 A | 8/1998 |
| JP | 11-504464 A | 4/1999 |
| JP | 11-340291 A | 12/1999 |
| JP | 2002-150990 A | 5/2002 |
| JP | 2004-245660 A | 9/2004 |
| JP | 2005-10014 A | 1/2005 |
| JP | 2005-214978 A | 8/2005 |
| WO | 99/13500 | 3/1999 |

* cited by examiner

FIG. 2 A
FIG. 2 B
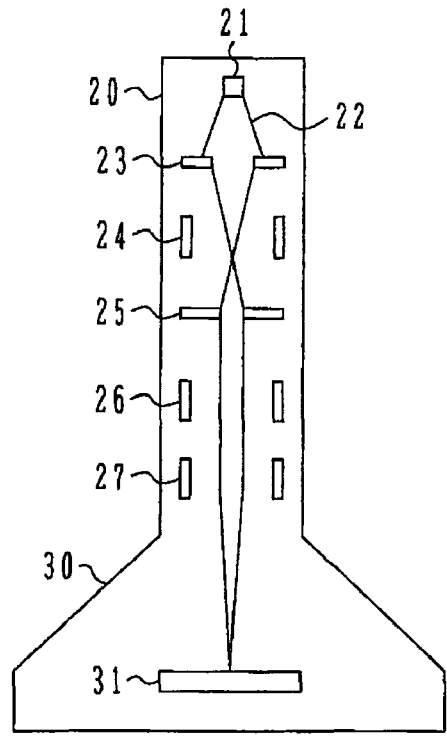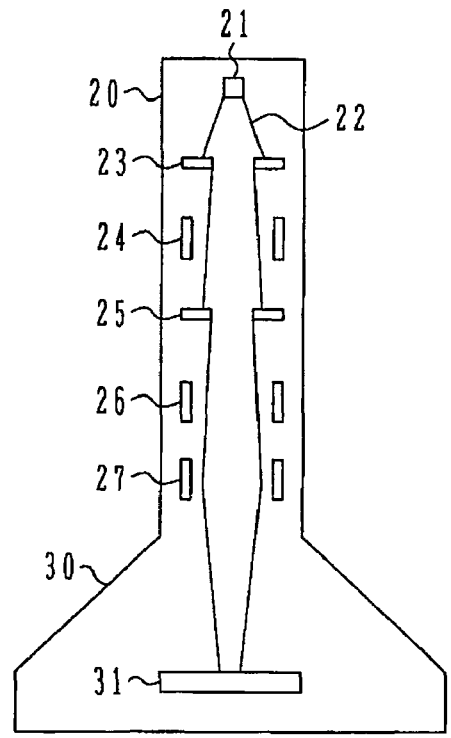
FIG. 3 A
FIG. 3 B
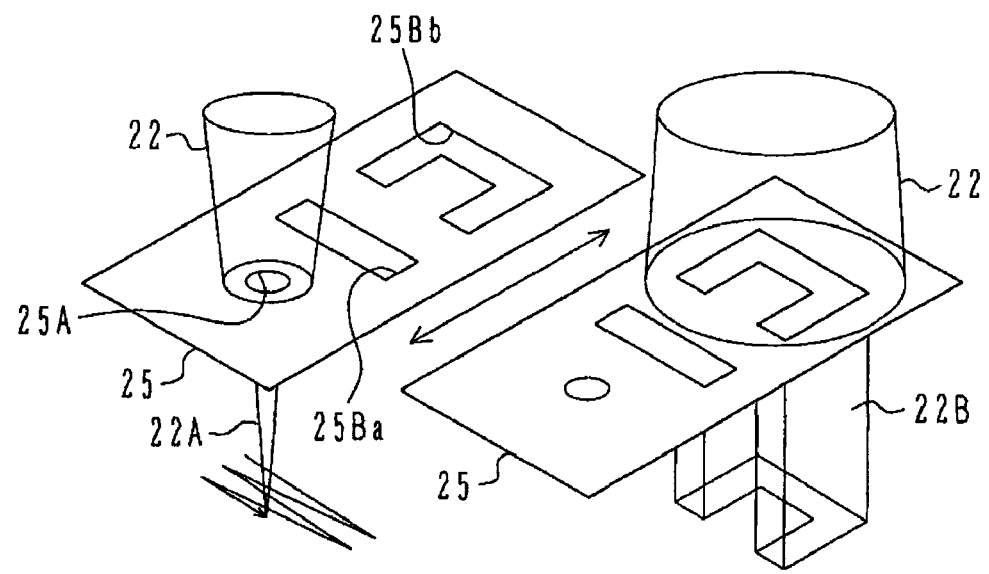

CHARGE PARTICLE BEAM SYSTEM, SAMPLE PROCESSING METHOD, AND SEMICONDUCTOR INSPECTION SYSTEM

BACKGROUND OF THE INVENTION

1. Field of the Invention

The present invention relates to a charged particle beam system for the inspection and analysis of a sample, a sample processing method, and a semiconductor inspection system.

2. Background Art

A typical example of the cause of defects that lead to a decrease in the yield of semiconductor devices, such as microprocessors and memories, is the attaching of particles to the sample (such as a wafer). The attachment of particles, such as an electrically conductive particle attaching between patterns to cause a short-circuit, or an insulative particle attaching to a connector portion of a wiring pattern to cause conduction failure, causes defective devices. Thus, it is necessary to identify the source of such particles and prevent their development. One method of identifying a source of particles is to analyze the elements of the particle to infer its cause. The method, ultimate analysis, can be performed by means of an energy dispersive X-ray (EDX) system, whereby a substance is irradiated with an electron beam to cause the substance to emit characteristic X-ray whose energy spectrum allows the identification of its elements.

Currently, for the detection of particles, optical inspection systems having a high throughput are generally employed. An optical inspection system includes a stage on which a sample is mounted. While the stage is moved, the sample surface is imaged with an optical microscope, or irradiated with laser light so as to detect scattered light on the sample surface, in order to provide a sample image, based on which adjacent cells or dice are compared to detect a defect portion.

The sample in which a defect has been detected by the optical inspection system is often handed over to a scanning electron microscope for analysis of the defect at higher resolution. The review SEM is a scanning electron microscope for defect analysis which is capable of auto defect review or auto defect classification; some review SEM's are equipped with the EDX functions. However, not every defect detected by the optical inspection system can be confirmed with the scanning electron microscope. For example, if a particle exists in a silicon oxide film or a transparent resist film, the scanning electron microscope can only obtain the information about the film surface and not the information about the particle inside the film, even if the particle inside the film has been established by the optical microscope. The inability of the SEM image to confirm the particle means that the location to be irradiated with an electron beam for ultimate analysis cannot be determined, so that the EDX functions cannot be taken advantage of.

Thus, when a particle inside a film is analyzed, an FIB (focused ion beam) processing system is used. Specifically, the film is machined until the particle or the like appears at the surface, and then the thus exposed particle is observed with an SEM or subjected to EDX analysis.

Currently, the ion source of an FIB generally employs a liquid metal ion source (LMIS), such as Ga (gallium). In the case of an FIB processing system using an LMIS, there is the problem of the LMIS becoming attached to the FIB irradiated surface of the sample, resulting in the development of contamination. Thus, samples that have been processed with an FIB have been unable to be returned to the production line and had to be discarded. In EDX analysis too, the LMIS creates a main cause of preventing an accurate ultimate analysis of a particle.

Another method to expose a particle in the film does not employ an FIB processing system but involves exposure and etching of the sample to process the film on the sample surface so as to expose the particle in the film (see Patent Document 1).

Patent Document 1: JP Patent Publication (Kokai) No. 11-340291 A (1999)

SUMMARY OF THE INVENTION

When the sample surface is processed using exposure and etching in order to analyze the particle in the film, although the problem of contamination by the LMIS can be avoided, the method is troublesome and leads to a decrease in yield.

It is therefore an object of the invention to provide a charged particle beam system, a sample processing method, and a semiconductor inspection system capable of accurately detecting a particle in a film without causing LMIS contamination and allowing quick observation with an electron microscope.

In order to achieve the aforementioned object, in accordance with the invention, a particle detected by an optical inspection system that exists in a film and that causes a defect is detected by an optical microscope based on position information acquired by the optical inspection system, and the sample is processed using a nonmetal ion beam so that the particle can be observed on an electron microscope image or an ion microscope image.

EFFECTS OF THE INVENTION

The invention makes it possible to observe the shape of a particle in a film that cannot be observed with an SEM image. As a result, the sample can then be processed, as needed, for EDX analysis, thereby allowing to infer the cause of development of the particle in a short time.

BRIEF DESCRIPTION OF THE DRAWINGS

FIG. 2 illustrates differences between different ion beam modes.

FIG. 3 shows the positional relationship between the beam mode and a mask.

DESCRIPTION OF THE PREFERRED EMBODIMENTS OF THE INVENTION

In the following, embodiments of the invention are described with reference to the drawings.

Figure 1:
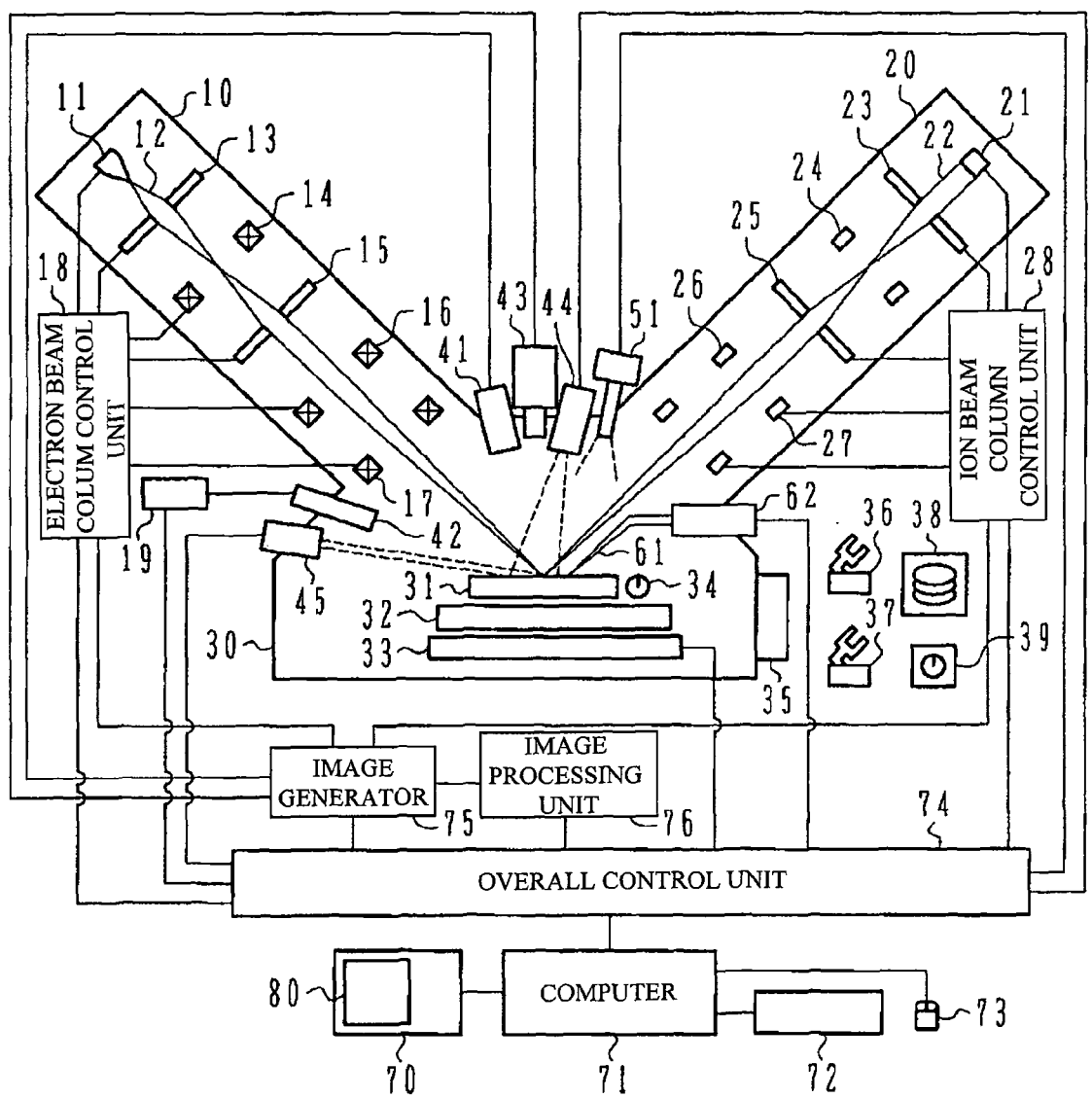
FIG. 1 schematically shows the overall structure of a semiconductor inspection system according to an embodiment of the invention.

FIG. 1 shows a schematic diagram of an embodiment of a semiconductor inspection system of the invention.

The semiconductor inspection system of the present embodiment comprises a sample holder 32 holding a sample (such as a wafer) 31, and a sample chamber 30 that encloses a sample stage 33 on which the sample holder 32 is mounted and that is movable.

The sample holder 32 is provided, outside the region in which the sample 31 is held, with a cartridge unit 40 (see FIG. 6) for holding a cartridge 34 on which a piece of sample (microsample) 93 (to be described later) cut out of the sample 31 is mounted. The cartridge unit 40 is capable of rotating the cartridge 34 about its axis so as to adjust the angle of incidence of an ion beam or the like onto the microsample.

The sample stage 33 can be moved along the x axis and the y axis in the horizontal plane, and along the z axis in the vertical direction, while maintaining the horizontal position in the horizontal plane. The sample stage 33 may be provided with functions, as needed, for inclining the surface of the mounted sample 31 from the horizontal position with respect to the horizontal plane, or rotating it about an axis perpendicular to the sample-mounting plane of the sample holder. When the sample 31 on the sample holder 32 is irradiated with an electron beam or an ion beam, the inside of the sample chamber 30 is maintained at vacuum by a vacuum system, which is not shown.

The sample chamber 30 has connected thereto the following: an electron beam column (SEM column) 10 having an electron beam optical system for focusing an electron beam 12 with which the surface of the sample 31 on the sample holder 32 is scanned and irradiated; a secondary electron detector 41 for detecting secondary electrons emitted by the sample 31 as it is irradiated with the electron beam 12; an X-ray detector 42 for detecting characteristic X-ray emitted by the sample 31 as it is irradiated with the electron beam 12; an ion beam column 20 having an ion beam optical system for irradiating the surface of the sample 31 on the sample holder 32 with an ion beam 22; a bright field light source 44 for irradiating the surface of the sample 31 on the sample holder 32 with illuminating light for producing a bright field image with an optical microscope 43 and an optical microscope 43; a dark field light source 45 for irradiating the surface of the sample 31 on the sample holder 32 with illuminating light for producing a dark field image with an optical microscope 43; a deposition gas source 51 for providing a deposition gas for forming a deposition film upon beam irradiation; a probe transfer mechanism 62 for moving a probe 61 for extracting a piece of sample (microsample) from the sample 31; and a sample exchange chamber 35 for loading and unloading the sample 31 and the cartridge 34 into and out of the sample chamber 30 without adversely affecting the vacuum in the sample chamber 30.

The optical microscope 43 is disposed at a position allowing the observation of the region (near the beam target position) irradiated with the ion beam 22. The bright field light source 44 and the dark field light source 45 are disposed such that they irradiate a substantially identical area with their illuminating light.

Figure 5:
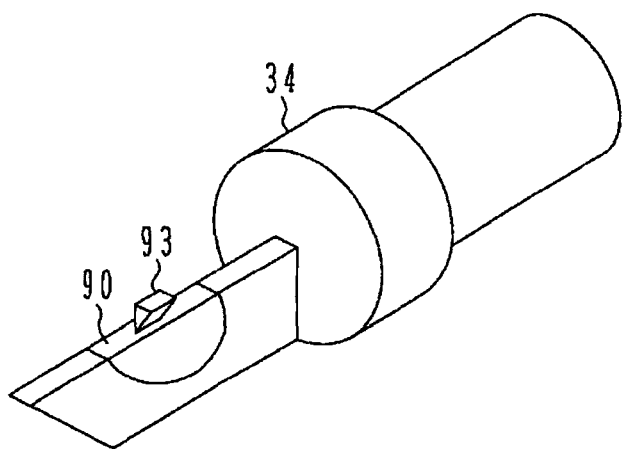
FIG. 5 shows the structure of a cartridge.
Figure 6:
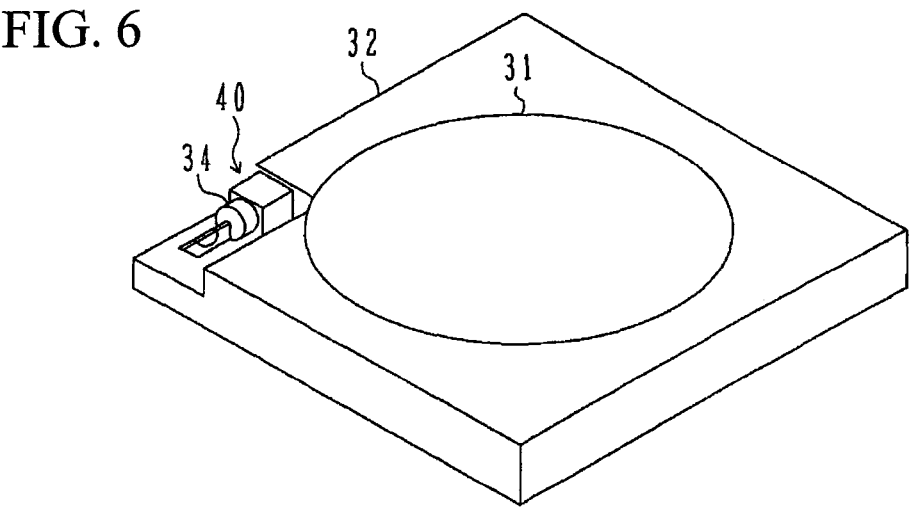
FIG. 6 shows the structure of a sample holder.

FIG. 5 shows the structure of the cartridge 34. FIG. 6 shows the structure of the sample holder 32. The cartridge 34 holds a sample carrier 90 for immobilizing a piece of sample 93 extracted from the sample 31; the cartridge 34 functions as a vessel for transporting the piece of sample 93 to a high resolution analytical system. A cartridge transfer robot 37 (see FIG. 1) removes the cartridge 34 from a cartridge case 39 (see FIG. 1) and transfers it above the sample holder 32 within the sample exchange chamber 35, which is adjusted to the atmospheric condition. The sample transfer robot 36 (see FIG. 1) also transfers a sample 31 stored in a sample case 38 (see FIG. 1) that has been inspected for defect in a separate optical inspection system above the sample holder 32, which is kept standing by in the sample exchange chamber 35 of the atmospheric condition. In this way, the sample holder 32 can mount the cartridge 34 as well as the sample 31. Furthermore, the sample holder 32 has incorporated therein a mechanism to rotate the cartridge 34 about its central axis so as to incline the retained piece of sample 93. After the sample exchange chamber 35 is evacuated, the sample holder 32 on which the sample 31 and the cartridge 34 are mounted is transported above the sample stage 33 in the sample chamber 30.

Referring back to FIG. 1, the deposition gas supplied by the deposition gas source 51 consists of tetraethylorthosilicate (TEOS), for example. TEOS dissolves upon beam irradiation to form a silicon oxide film.

The electron beam optical system in the electron beam column 10 focuses the electron beam 12, which is drawn from the electron source 11, onto the sample 31 held on the sample holder 32 so as to scan the sample with the beam. The electron beam optical system includes: an extraction electrode 13 for drawing the electron beam 12 from the electron source 11; a focusing lens 14 for focusing the electron beam 12 drawn by the extraction electrode 13; a beam aperture 15 for narrowing the size of the focused electron beam 12; a deflector 16 for deflecting the electron beam 12 for scanning; and an objective lens 17. Upon activation of the system, the inside of the electron beam column 10 communicated with the sample chamber 30 is maintained at high vacuum, together with the sample chamber 30.

The ion beam optical system in the ion beam column 20 is used for irradiating the sample 31 held on the sample holder 32 with the ion beam 22 drawn from the nonmetal gas ion source 21. The ion beam optical system includes: an extraction electrode 23 for drawing the ion beam 22 from the gas ion source 21; a focusing lens 24 for focusing the ion beam 22 drawn by the extraction electrode 23; a mask 25 for shaping the cross section of the focused ion beam 22; a deflector 26 for deflecting the ion beam 22; and an objective lens 27. Upon activation of the system, the inside of the ion beam column 20 in communication with the sample chamber 30 is maintained at high vacuum together with the sample chamber 30.

The semiconductor inspection system of the present embodiment comprises the following control systems: an electron beam column control unit 18 for controlling the electron beam column 10; an ion beam column control unit 28 for controlling the ion beam column 20; and an overall control unit 74 for controlling the constituent elements other than the both columns 10 and 20, such as the sample stage 33, the bright field light source 44, the dark field light source 45, the deposition gas source 51, and the probe transfer mechanism 62.

Image data, such as an electron microscope image (in the present case, an SEM image) provided by the electron beam column 10, an ion microscope image (SIM image) provided by the ion beam column 20, and an optical microscopic image provided by the optical microscope 43, is generated by an image generator 75. For example, the image generator 75 generates the image data for the SEM image from a detection signal of secondary electrons provided by the secondary electron detector 41 during irradiation with the electron beam 12, in synchronism with the scan signal for the electron beam provided by the electron beam column control unit 18. The image generator 75 generates the image data for the SIM image from the detection signal of secondary electrons provided by the secondary electron detector 41 during irradiation with the ion beam 22, in synchronism with the scan signal for the ion beam provided by the ion beam column control unit 28. The image generator 75 generates the image data for the optical microscopic image taken by the optical microscope 43 based on image data provided by the optical microscope 43. The individual pieces of image data thus generated are fed to the image processing unit 76, which compares the image data between adjacent regions (in the cell or die units) in the semiconductor device to detect a defect portion based on their difference.

The semiconductor inspection system of the present embodiment also comprises a computer 70 having a display device 70 for displaying various microscopic images reconstructed from the above image data, and operating devices such as a keyboard 72 and a mouse 73.

In the gas ion source 21 of the ion beam column 20, nonmetal gas, such as oxygen or argon, is transformed into a plasma for the production of the ion beam 22. The ion beam 22 produced by the gas ion source 21 is a wide projection beam. In the above ion beam column control unit 28, at least two beam modes are stored as programs for the ion beam focusing operation to be instructed to the ion beam column 20.

A first beam mode is a mode in which, as shown in FIG. 2(a), the ion beam narrowed by the focusing lens 24 is passed through a circular mask sharp 25A (see FIG. 3) in the mask 25, deflected by the deflector 26 for scanning, and then focused by the objective lens 27 onto the sample 31. A scanning ion beam 22A (see FIG. 3) is the ion beam in this first beam mode. This scanning ion beam 22A is used for determining the position on the sample 31 or the like where processing is to be conducted with the processing ion beam 22B (see FIG. 3).

In the second beam mode, as shown in FIG. 2(b), the beam is passed through a mask sharp 25Ba or 25Bb of the mask 25 without narrowing the beam with the focusing lens 24, so as to shape the beam cross-section in the shape of the mask sharp 25Ba or 25Bb to provide a projection beam that is reduced in size and projected by the objective lens 27 for processing. The ion beam in this second beam mode is a processing ion beam 22B. In this second beam mode, the beam current for the processing ion beam 22B can be increased compared with the scanning ion beam 22A, so that processing speed can be increased compared with the case of using the ion beam of the first beam mode as the processing ion beam.

The mask 25 provided in the ion beam column 20 consists of apertures as shown in FIG. 3, having the circular mask sharp 25A for scanning ion beam and the mask sharps 25Ba and 25Bb adapted to the processed shapes for the processing ion beam. The mask sharp 25Ba is rectangular and is used for obtaining a processing ion beam 22Ba having a rectangular cross section (see FIG. 19). The mask sharp 25Bb is Π-shaped and is used to obtain a processing ion beam 22Bb (see FIG. 18) having a Π-shaped cross section. The beam mode is set by moving the mask 25 in the direction of the arrow in FIG. 3 using a drive mechanism, which is not shown. The number of the mask openings and their shapes are not limited to those shown in FIG. 3.

FIG. 3(a) illustrates the first beam mode in which the scanning ion beam 22A is radiated.

As shown in FIG. 3(a), in the first beam mode, the ion beam 22 is narrowed by the focusing lens 24 to have a diameter slightly greater than the diameter of the mask sharp 25A. The scanning ion beam 22A that has passed through the mask 25 is scanned by the deflector 26 and then focused by the objective lens 27 onto the sample 31.

FIG. 3(b) illustrates the second beam mode in which the processing ion beam 22B is radiated.

As shown in FIG. 3(b), in the second ion beam mode, without narrowing the ion beam 22 with the focusing lens 24, the ion beam 22 of such a diameter as to cover the mask sharp 25Ba or 25Bb (25Bb in the present example) of the mask 25 for processing ion beam shaping is irradiated. The processing ion beam 22B that has passed through the mask sharp 25Ba or 25Bb is reduced in size and projected by the objective lens 27 onto the sample 31 while correcting its position with the deflector 26.

Example 1

Figure 4:
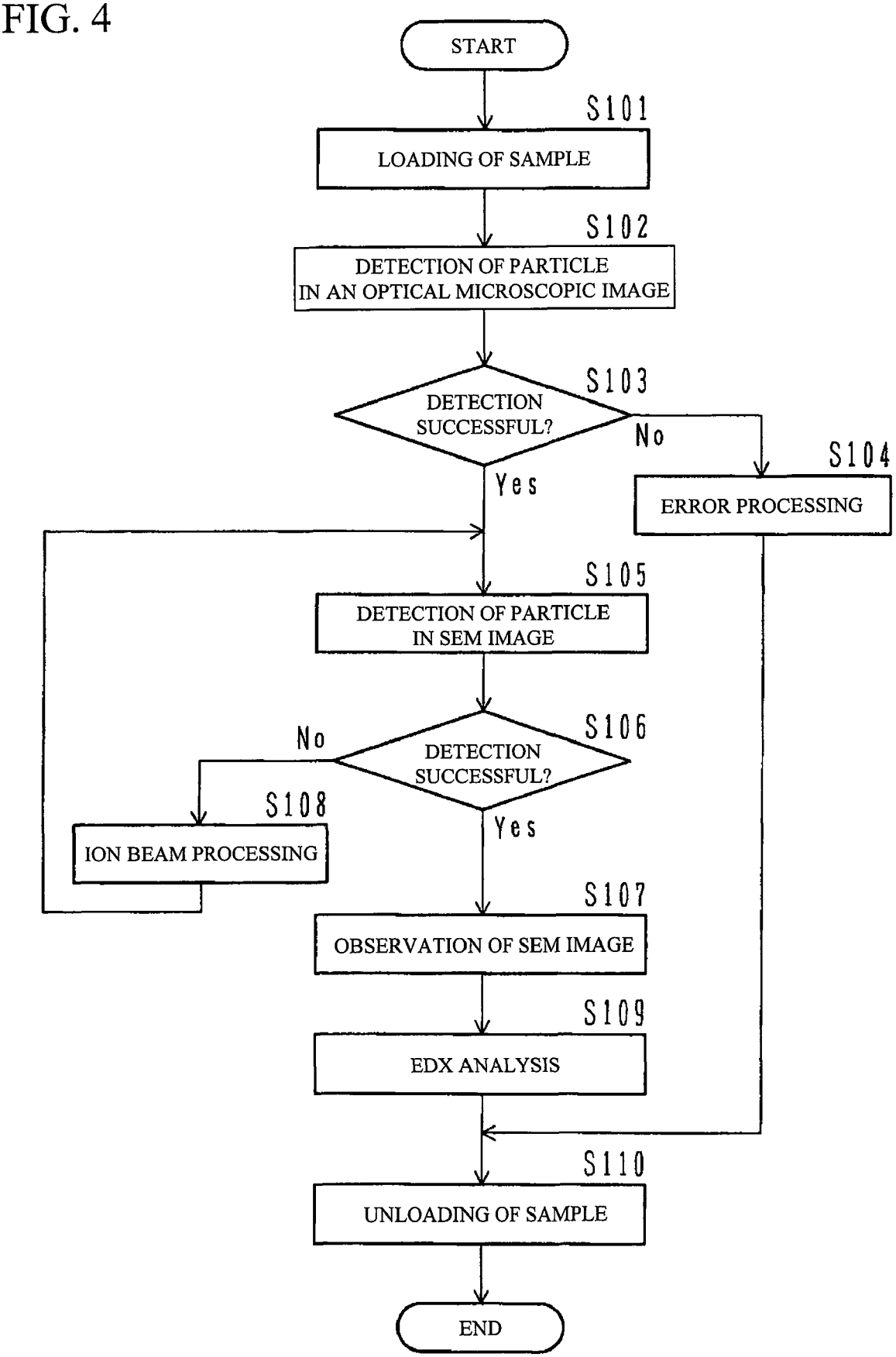
FIG. 4 shows a flowchart of a first example of a procedure for analyzing (reviewing) a defect portion of a sample that has been detected with a separate optical inspection system, using the semiconductor inspection system of the present embodiment.

FIG. 4 shows a flowchart of a first example of the procedure for analyzing (reviewing) a defect portion of a sample detected by a separate optical inspection system, using the semiconductor inspection system of the present embodiment.

In the following, the defect analysis procedure using the semiconductor inspection system of the present embodiment is described with reference to FIG. 4.

When the semiconductor inspection system of the present embodiment is used for the wafer defect inspection in a semiconductor device manufacturing process, the sample (wafer) 31 is loaded in step S101. Prior to loading, the sample 31 that has been subjected to defect inspection by the separate optical inspection system is stored in the sample case 38 in advance and mounted on the load port.

Upon instruction from the computer 71 to start inspection with the sample 31 stored in the sample case 38, the overall control unit 74 outputs an instruction signal to the sample transfer robot 36 to take out the sample 31 from the sample case 38 and transport it above the sample holder 32, which stands by within the sample exchange chamber 35 in the atmospheric condition. The overall control unit 74 also outputs an instruction signal to the cartridge transfer robot 37 to take out the cartridge 34 from the cartridge case 39 and transfer it above the sample holder 32 within the sample exchange chamber 35 of the atmospheric condition. The sample 31 and the cartridge 34 are then mounted on the sample holder 32 (see FIG. 6). The overall control unit 74 then outputs an instruction signal to the vacuum system (not shown) to evacuate the sample exchange chamber 35. Thereafter, the sample holder 32 with the sample 31 and the cartridge 34 mounted thereon is transferred above the sample stage 33 within the sample chamber 30.

Next, in step S102, upon instruction to acquire an optical microscopic image of the defect that has been detected in advance by the separate optical inspection system so as to confirm the defect, the overall control unit 74, in response to an operating signal, outputs an instruction signal to the sample stage 33 to be transferred such that the defective site enters the field of view of the optical microscope 43. An inspection result file indicating the position of the defective site detected by the separate optical inspection system is transferred from the optical inspection system to the computer 71 via a network or the like. The overall control unit 74, based on the inspection result file, selectively turns on the bright field light source 44 or the dark field light source 45 depending on the conditions upon detection by the optical inspection system, and then a sample image is photographed with the optical microscope 43.

Figure 7:
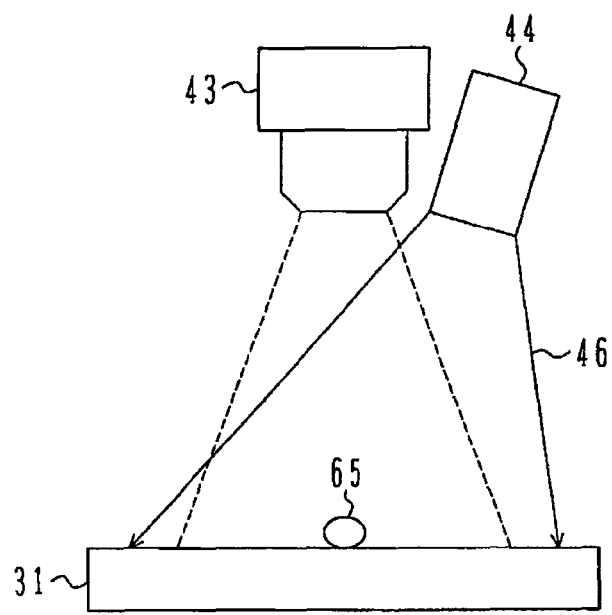
FIG. 7 shows the principle of acquisition of a bright field optical microscopic image.

FIG. 7 illustrates the principle of acquisition of a bright field optical microscopic image.

Figure 8:
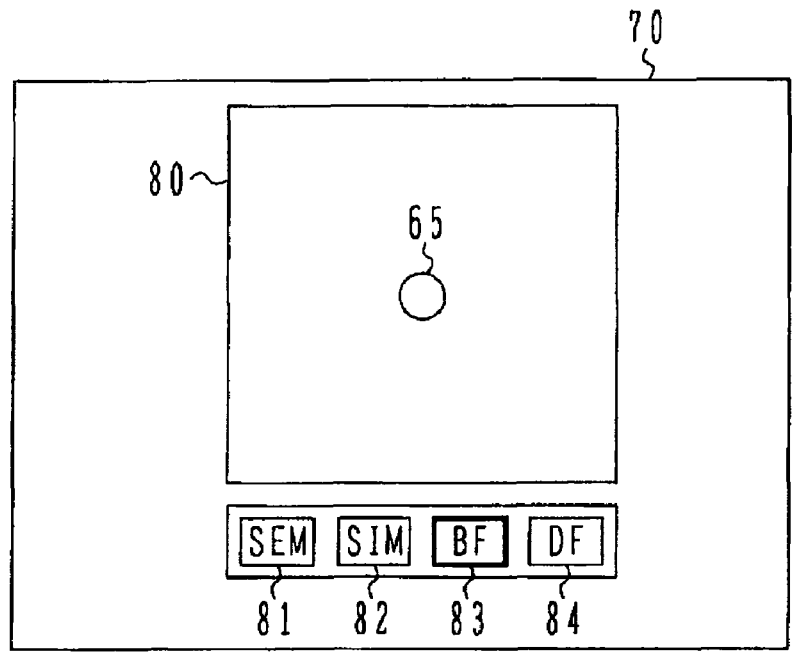
FIG. 8 shows a bright field optical microscopic image on display.

As shown in FIG. 7, when a bright field optical microscopic image is to be obtained with the optical microscope 43, the sample 31 is irradiated with the illuminating light 46 produced by the bright field light source 44 and then a particle (defect) 65 on the sample 31 is imaged with the optical microscope 43. The image data is processed in the image generator 75 to produce a bright field optical microscopic image, which is then displayed in the image display area 80 of the display device 70 by operating a BF button 83 provided in the display device 70 to instruct such display, as shown in FIG. 8.

Figure 9:
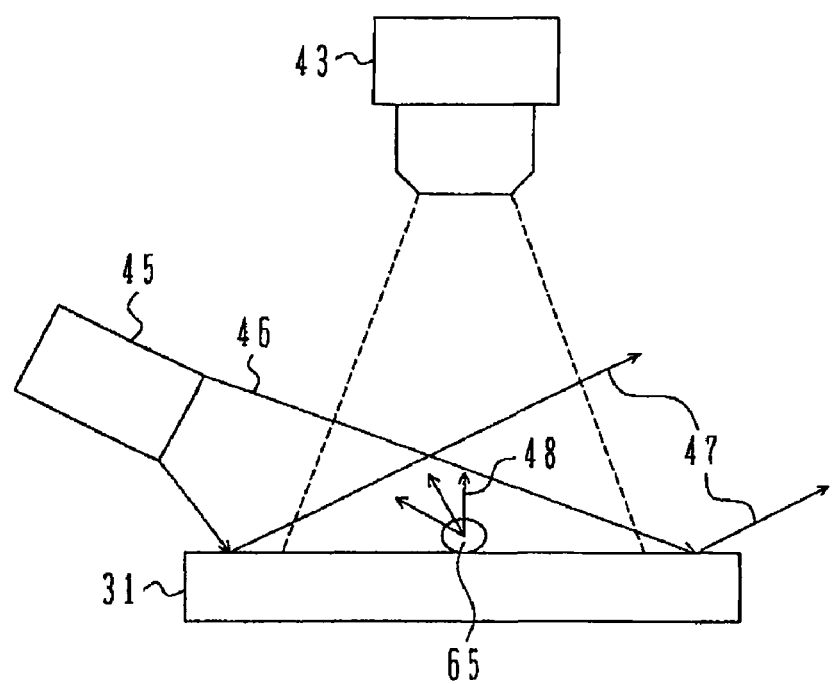
FIG. 9 shows the principle of acquisition of a dark field optical microscopic image.

FIG. 9 illustrates the principle of acquisition of a dark field optical microscopic image.

Figure 10:
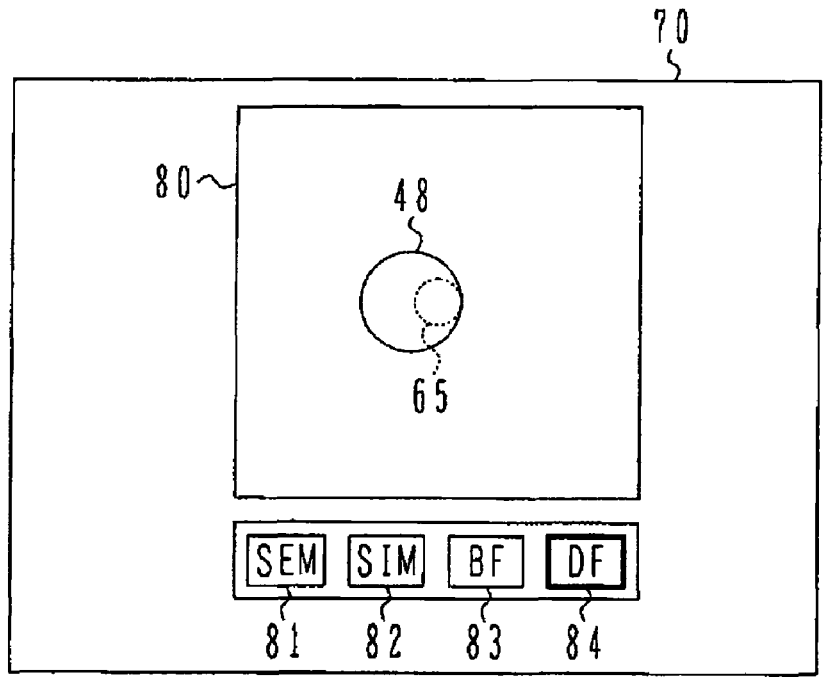
FIG. 10 shows a dark field optical microscopic image on display.

As shown in FIG. 9, when a dark field optical microscopic image is to be obtained with the optical microscope 43, the sample 31 is irradiated with the illuminating light 35 from the dark field light source 45, which is disposed at a position such that the reflected light 47 of the illuminating light 46 does not become incident on the optical microscope 43. Then, the scattered light 48 caused by the particle 65 on the sample 31 is imaged with the optical microscope 43. The imaged data is processed in the image generator 75 to produce a dark field optical microscopic image, which is displayed in the image display area 80 of the display device 70 by operating a DF button 84 provided in the display device 70 for instructing such display, as shown in FIG. 10.

The sample image (a bright field optical microscopic image or a dark field optical microscopic image) obtained by the optical microscope 43 is then fed to the image processing unit 76. The image processing unit 76 compares adjacent regions (in units of cells or dice) of the image to detect a defect portion. Upon successful detection of a particle in the optical microscopic image, a step S105 is carried out to detect the particle on an SEM image. If the particle detection was unsuccessful, an error process is carried out in step S104, followed by a step S110 where the sample 31 is loaded out of the apparatus to end the present analysis procedure.

In step S105, the electron beam column 10 is controlled by the electron beam column control unit 18 to acquire an electron microscope image (SEM image) of the defect detected by the optical microscope 43, in an attempt to detect the defect on an SEM image.

Figure 11:
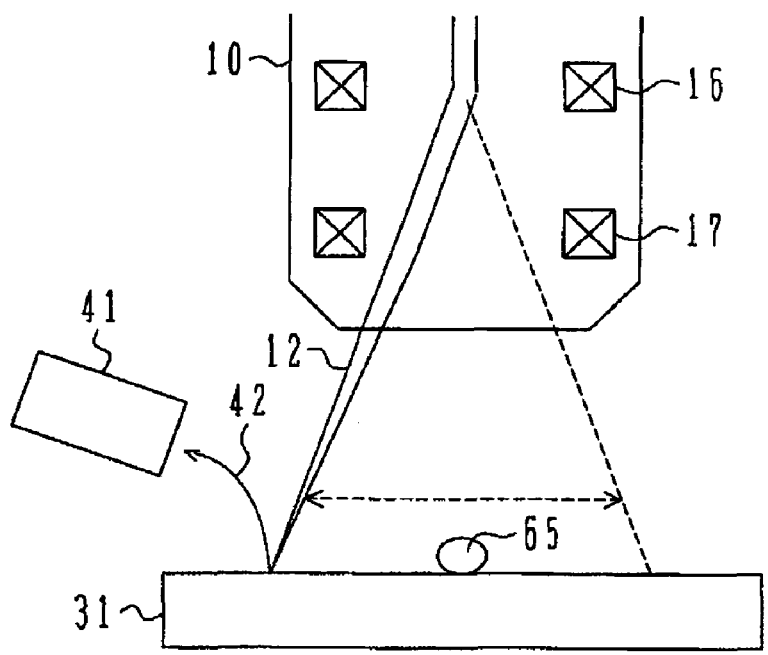
FIG. 11 shows the principle of acquisition of an SEM image.

FIG. 11 illustrates the principle of acquisition of an SEM image.

Figure 12:
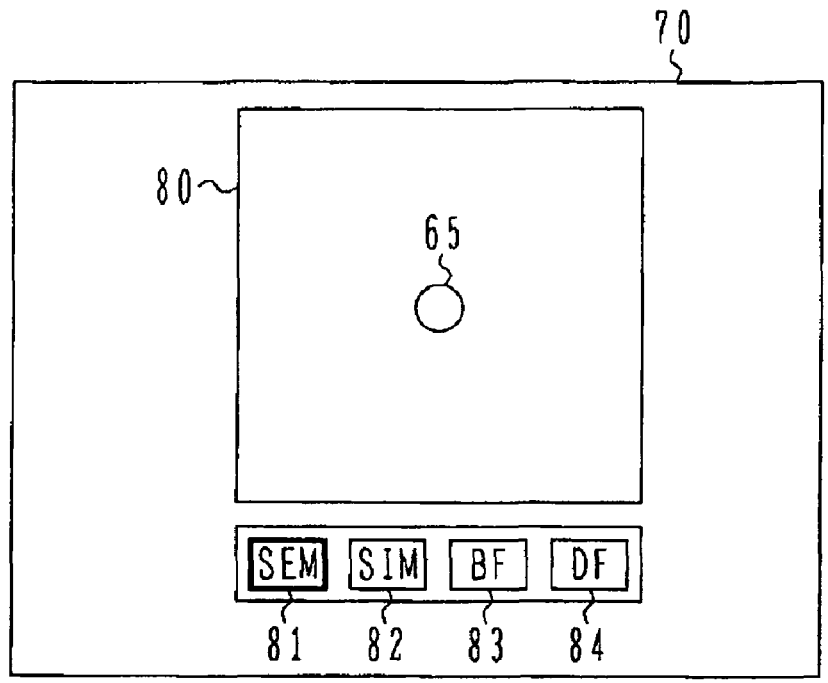
FIG. 12 shows an SEM image on display.

As shown in FIG. 11, when an SEM image is to be acquired using the electron beam column 10 and the secondary electron detector 41, the sample 31 is scanned with the electron beam 12 outputted by the electron beam column 10 and the secondary electron that are generated are detected with the secondary electron detector 41. The signal from the secondary electron detector 41 is taken in synchronism with the scan signal for the electron beam 12, and then an SEM image is generated by the image generator 75. The generated SEM image is displayed in the image display area 80 of the display device 70 by operating an SEM button 81 provided in the display device 70 to instruct such display, as shown in FIG. 12. The image processing unit 76 compares adjacent regions (in units of cells or dice) in the SEM image to detect the defective site.

Figure 13:
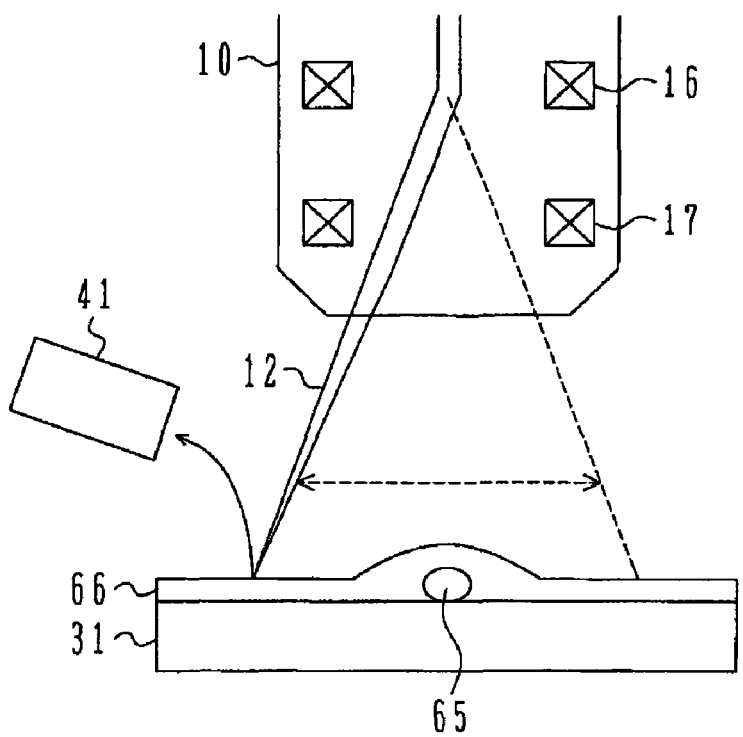
FIG. 13 illustrates how an SEM image of a particle in a film is acquired.
Figure 14:
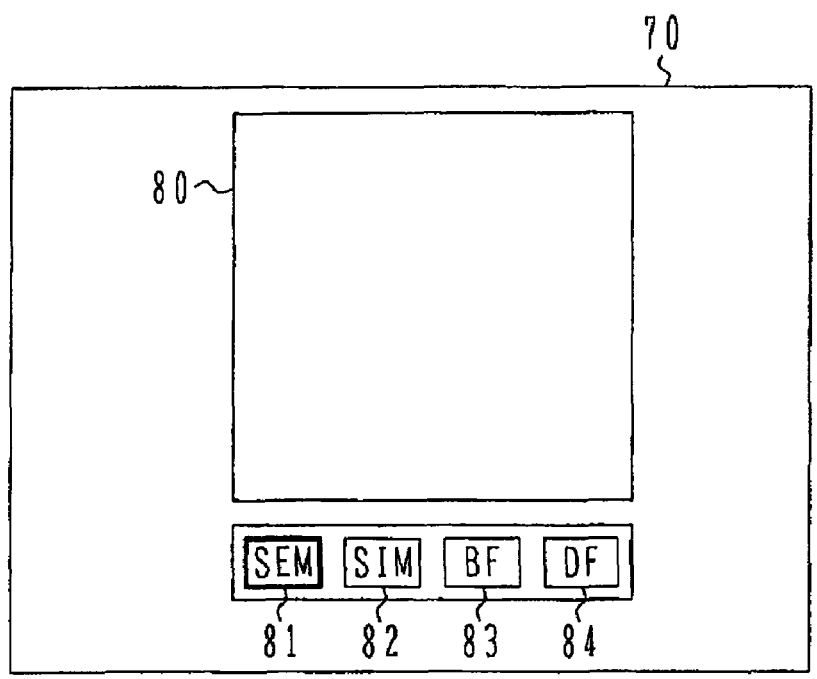
FIG. 14 shows an SEM image of the particle in the film that is displayed.

In step S106, it is determined whether or not the defective site detected by the optical microscope 43 has been successfully detected in the SEM image. If the detection of the particle in the SEM image has been successful, the routine proceeds to step S107 where the particle in the SEM image is observed; if unsuccessful, the sample is processed with the ion beam in step S108. One of the causes of failure to detect the defective site via the SEM image is when the particle 65 exists in the film 66, as shown in FIG. 13. Since the SEM only allows the acquisition of information about the sample surface, if the defective site is covered with the film 66 and if the sample surface is gradual, the particle 66 that has been detected in the optical microscopic image is not necessarily detectable with the SEM image. Therefore, there are cases in which the particle 66 is not displayed in the SEM image in the image display area 80 of the display device 70, as shown in FIG. 14.

Figure 15:
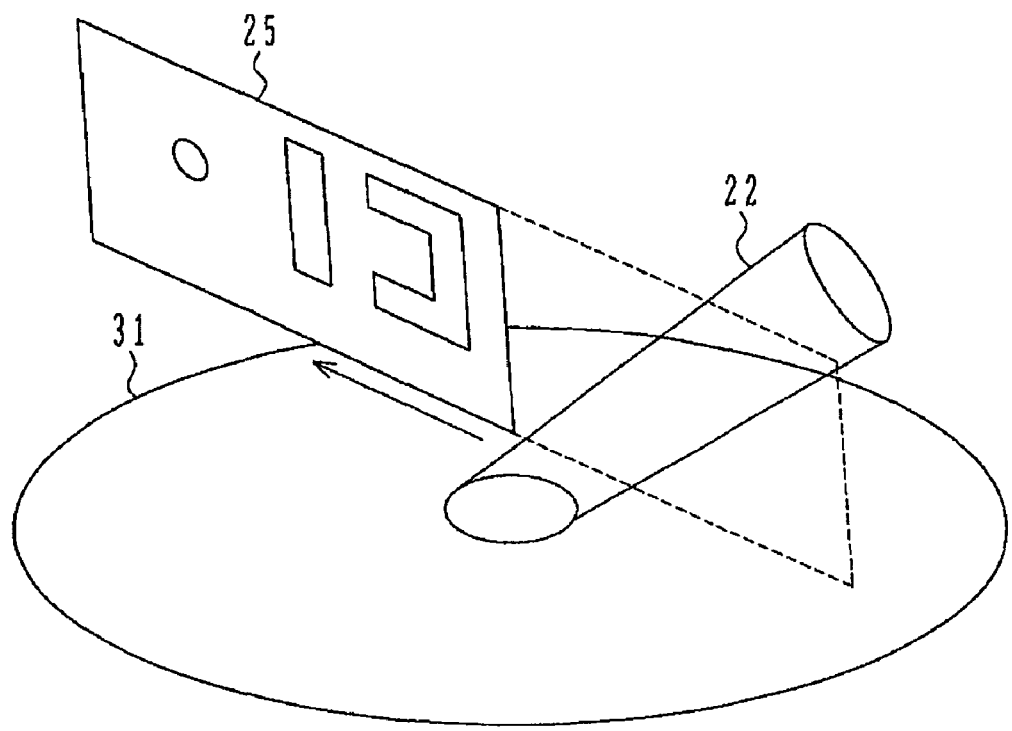
FIG. 15 shows the positional relationship between the mask and the ion beam.
Figure 16:
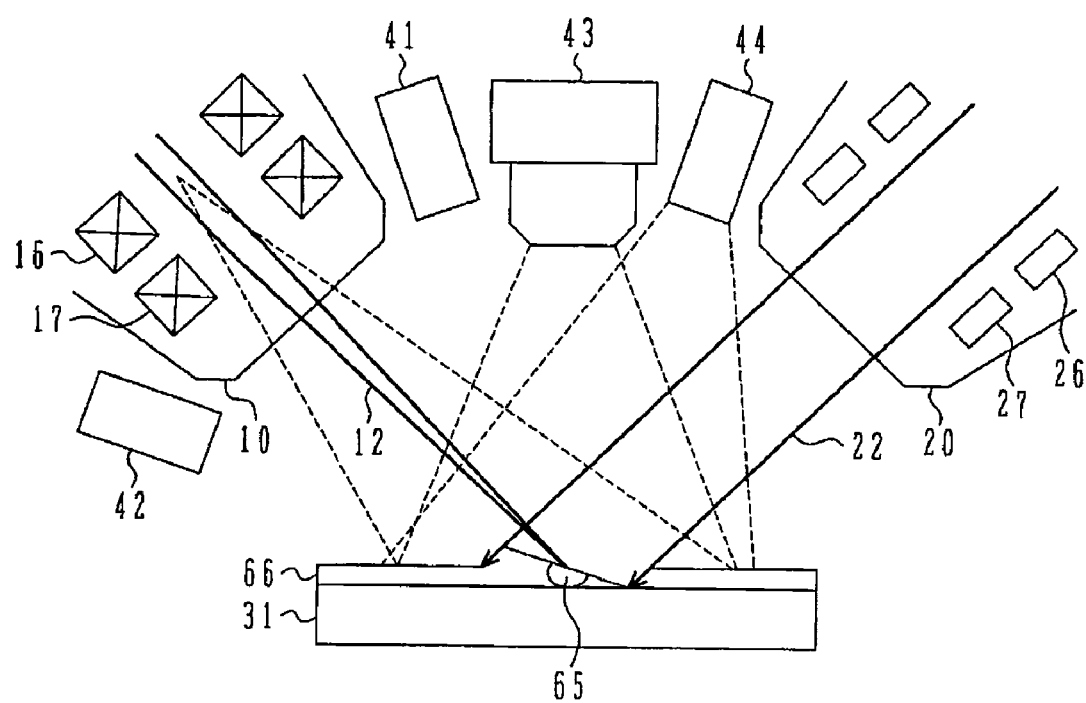
FIG. 16 illustrates how the film that covers the particle is removed with the ion beam.

If the detection of the particle in the SEM image has been unsuccessful, the routine proceeds to step S108 where the ion beam column 20 is controlled by the ion beam column control unit 28 and the film 66 is processed with the ion beam, while monitoring the bright field optical microscopic image (or the dark field optical microscopic image), so as to expose the particle 65 on the surface. When the particle 65 is thus exposed by machining the film 66 without extracting the particle from the sample 31, the mask 25 is withdrawn from the ion beam 22 as shown in FIG. 15, and then a wider ion beam of which the beam cross section has not been limited by the mask opening is used. In this way, a wider area can be processed at high speed. Furthermore, as shown in FIG. 16, the region irradiated with the ion beam 22 is scanned with the electron beam 12 so as to detect the secondary electron signal with the secondary electron detector 41, so that the progress of SEM image processing can be monitored with the SEM column as needed. In this way, the ion beam processing can be terminated upon exposure of the particle 65 (S105, S106).

Upon successful acquisition of an SEM image of the defective site, the particle 65 is observed in detail in step S107 in an SEM image at a higher magnification. In step S109, the X-ray obtained by irradiating the particle 65 with the electron beam 12 is detected with the X-ray detector 42 to perform ultimate analysis using an EDX. In this way, the elements of the particle 65 are identified and the source of its origin can be inferred. After the particle 65 has been analyzed, the routine proceeds to a step S110, where the overall control unit 74 causes the sample 31 to be loaded into the sample case 38 via the sample exchange chamber 35 in a procedure opposite to that in S101, whereupon the procedure ends.

In the following, the advantageous effects of the present embodiment are described.

Generally, for the detection of a defective site in a sample, an optical inspection system having a high throughput is used. Upon detection of a defect with the optical inspection system, the detected defective site is normally observed with an electron microscope, such as an SEM, so as to observe the defective site via an image having a higher resolution.

However, even if the sample in which a defect has been detected by the optical inspection system is delivered to the SEM in an attempt to obtain an SEM image of the defective site, if the defective site (such as the particle 65 attached to the wafer surface) is covered with a film, as described above with reference to FIGS. 13 and 14, no particle can be conformed in the SEM image even if the areas near the defective site is observed with the SEM on the basis of the position information supplied by the optical inspection system. This is because the SEM is only capable of acquiring information about the sample surface (i.e., the film). Furthermore, while it is necessary to expose the particle in order to perform ultimate analysis of the particle, it is difficult to obtain an SIM image of the particle within the film. Thus, the functions of the EDX cannot be readily utilized. It goes without saying that no observation with an TEM or a STEM is possible unless FIB processing can be conducted.

In contrast, in accordance with the present embodiment, even when a particle is present within a film and cannot be captured in an SEM image, since the particle is captured with the optical microscope 43 prior to SEM observation, the particle in the film can be exposed by removing the film by irradiating the position thereof at which the particle has been captured in the optical microscopic image with an ion beam.

For example, a film that covers a particle can be reliably removed by performing FIB processing while monitoring an optical microscopic image. Alternatively, the ion beam target position and the particle may be aligned with each other on the optical microscopic image (or the ion beam target position can be aligned with the coordinates of the particle detected by the optical microscope 43) prior to FIB processing, so as to ensure that the film with which the particle is covered is reliably processed by the FIB. Then, FIB processing can be performed while observing the sample with the SEM, and then the FIB processing can be terminated immediately upon confirmation of the particle in the SEM image (or the SIM image), i.e., upon exposing of the particle. Further alternatively, the optical microscopic image and the SEM image (or the SIM image) may be simultaneously displayed in the display area 80 of the display device 70. In this way, FIB processing can be terminated upon exposing of the particle in an SEM image (or an SIM image) while the film is removed efficiently in view of an optical microscopic image.

Thus, in accordance with the present embodiment, a particle covered with a film can also be discovered easily and quickly using the optical microscope 43, so that, even when the electron microscope observation or EDX ultimate analysis of the defective site is not possible, the film can be removed highly accurately and quickly by FIB processing. Since a nonmetal element is used for the processing ion beam instead of an LMIS, such as Ga, no LMIS contamination of the sample develops due to FIB processing. Thus, it becomes possible to accurately detect a particle in the film and conduct electron microscopic observation or EDX analysis at high speed, and the cause of the development of the particle can be inferred in a short time and improved yield can be achieved.

Furthermore, since the ion beam is nonmetal, there is no LMIS contamination in the sample after FIB processing, so that the sample after FIB processing can be returned to the manufacturing process, which helps reduce the amount of discarded wafers. Even though the use of a nonmetal ion beam prevents the development of contamination, particles tend to become collected in the processed opening if the opening is left as is, depending on the size thereof. This provides a cause for later contamination; in such a case, the processed opening can be filled by deposition.

In the present example, since both a dark field optical microscopic image and a bright field optical microscopic image can be acquired by the optical microscope 43, one or the other image can be selected and used for the particular purpose or use. For example, a dark field optical microscopic image shows the object under investigation larger than it actually is, so the image is effective in detecting small particles; however, if the sample shape is such (e.g., gradual) that scattered light is difficult to obtain, the dark field optical microscopic image sometimes fails to provide a clear image. On the other hand, while a bright field optical microscopic image does not display the observed object larger than it actually is, as in the case of the dark field optical microscopic image, it enables the observation of the sample regardless of its surface shape. If the use of both is not presumed, either the bright field light source 44 or the dark field light source 45 may be omitted.

Example 2

Figure 17:
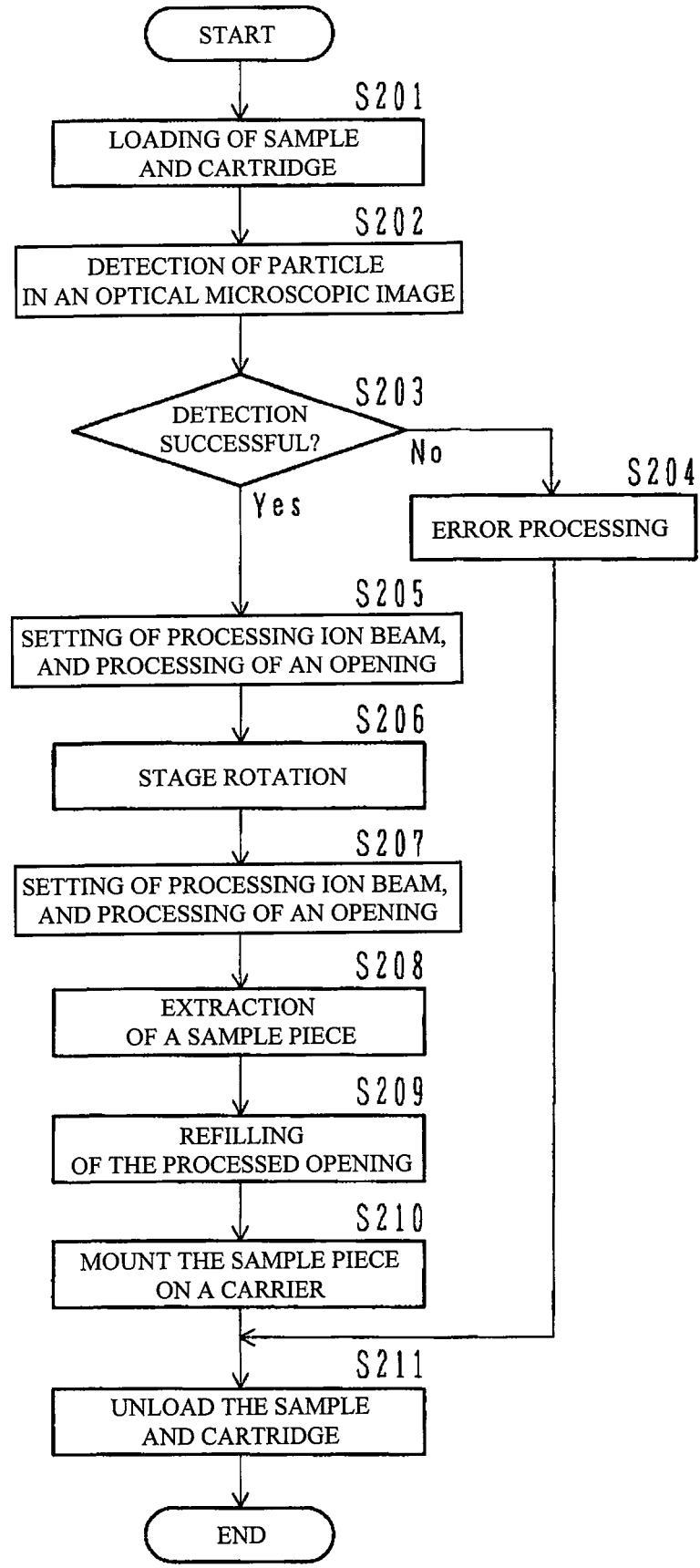
FIG. 17 shows a flowchart of a second example of the procedure for analyzing (reviewing) a defect portion in a sample that has been detected with the separate optical inspection system, using the semiconductor inspection system of the present embodiment.

FIG. 17 shows a flowchart of a second example of the procedure for analyzing (reviewing) the defect portion of a sample detected by a separate optical inspection system, using the semiconductor inspection system of the present embodiment.

The present example represents a process flow suitable for an accurate analysis of the particle 65 that exists in the film and that cannot be sufficiently observed by the SEM image by the scan of the electron beam 12 or by the SIM image by the scan of the ion beam 22, using a microscope image at higher resolution.

In the present example, the sample 31 and the cartridge 34 are mounted on the sample holder 32 in step S201, as described with reference to FIGS. 5 and 6, and then the sample holder is delivered into the sample chamber 30.

S202, S203, and S204 are the same as S102, 103, and 104 of FIG. 4. The defective site of the sample 31 delivered in the sample chamber 30 is detected by the optical microscope 43. If the defect detection by the optical microscopic image fails and the determination in S203 is not satisfied, the error process in S204 is carried out and the procedure moves to S211 where the sample 31 and the cartridge 34 are unloaded to end the analysis procedure of the present example.

Figure 18:
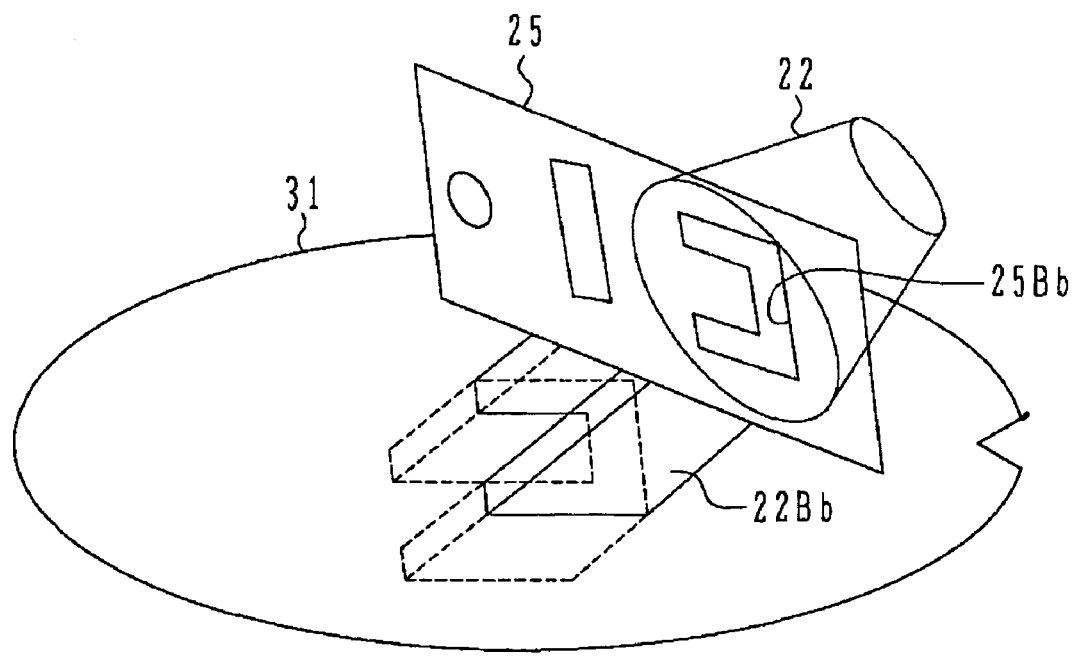
FIG. 18 shows the processing ion beam being used for processing.

On the other hand, if the defect detection by the optical microscopic image is successful and the determination in S203 is satisfied, the procedure moves to S205 where the beam mode is switched to the second beam mode, whereby, as shown in FIG. 18, the sample 31 is irradiated diagonally with the processing ion beam 22Bb having a Π-shaped cross section that has been passed through the mask sharp 25Bb of the mask 25, thereby forming a Π-shaped groove that surrounds the particle 65.

Figure 19:
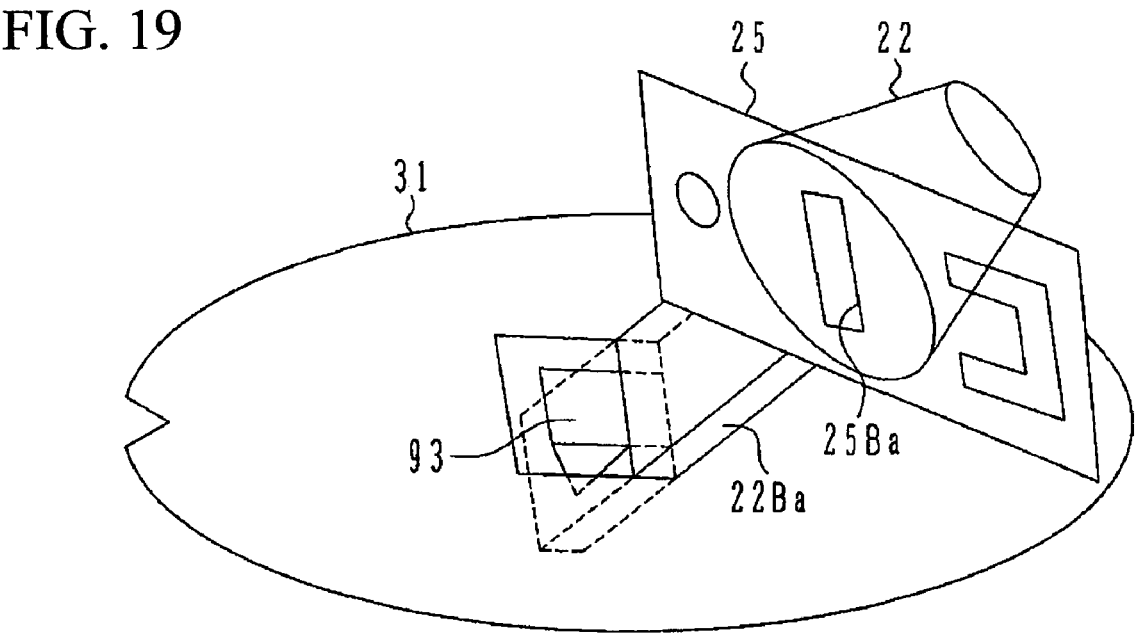
FIG. 19 shows the processing ion beam being used for processing.

In the following step S206, the sample stage 33 is rotated by 180° as shown in FIG. 19. Then, in step S207, the beam mode is switched to the first beam mode, whereby the sample 31 is diagonally irradiated with the processing ion beam 22Ba having a rectangular cross section that has been passed through the mask sharp 25Ba of the mask 25. As a result, a rectangular groove is formed to enclose the particle 65 together with the previously formed Π-shaped groove, and then a wedge-shaped piece of sample 93 is cut out. While it is also possible to cut out the piece of sample by combining the scan of the ion beam with the rotation/transfer functions of the stage 33, the use of the ion beam formed to the shape of a processed opening in advance can reduce the processing time.

Figure 20:
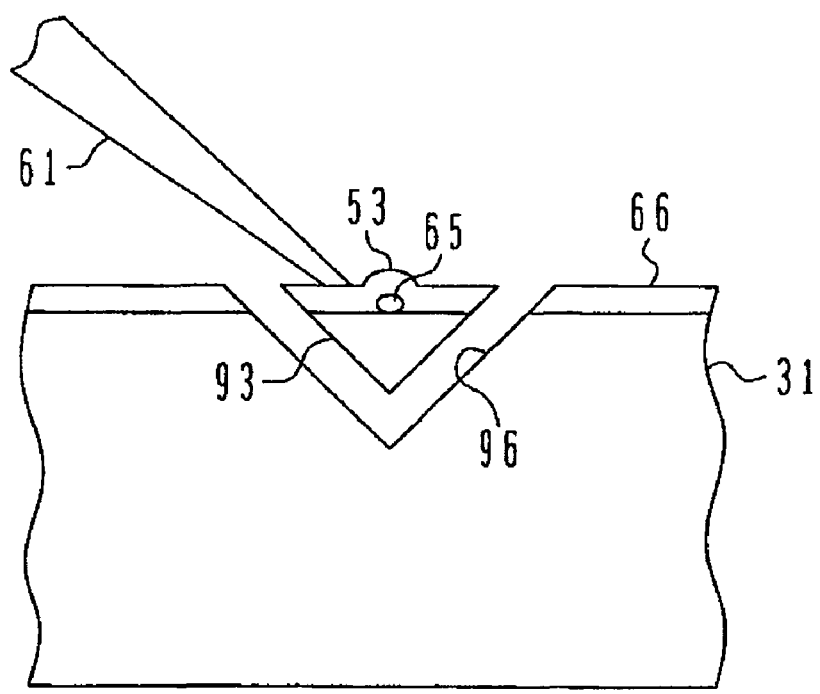
FIG. 20 illustrates how a piece of sample is extracted with the probe.

In S208, the piece of sample 93 separated from the sample 31 by the forming of the grooves is attached to the tip of the probe 61, as shown in FIG. 20, and then the probe 61 is raised to thereby extract the piece of sample 93. The piece of sample 93 is caused to become adsorbed on the probe 61 by electrostatic force. If the adsorbing force provided by the electrostatic force is too weak, the sample piece is bonded to the probe 61 via a deposition film formed by ion beam irradiation with the simultaneous supply of the deposition gas 52.

Figure 21:
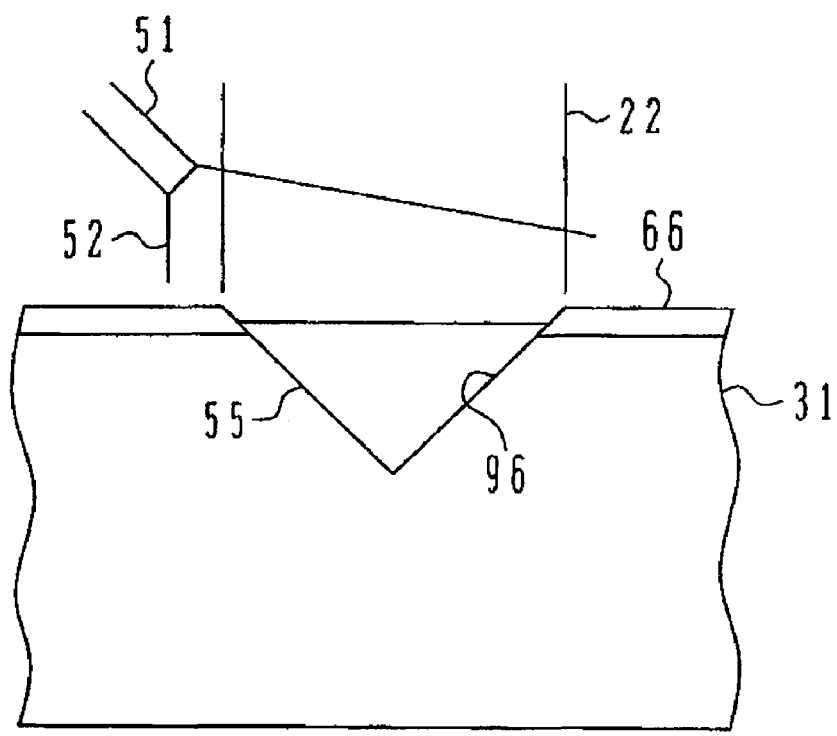
FIG. 21 shows the processed opening being filled up again.

In S209, the processed opening 96 that remains in the sample 31 after the piece of sample 93 is extracted is filled again. If the processed opening 96 after the extraction of the piece of sample 93 is left unfilled, particles tend to become collected in the processed opening 96, and to return such sample 31 with the remaining processed opening 96 to the production line might cause a problem in the subsequent step. Thus, in the procedure of S209, as shown in FIG. 21, the ion beam 22 is irradiated while the deposition gas 52 is supplied, so as to fill the processed opening 96 again. At this time, a mask sharp suitable for the filling of the processed opening 96 is selected for the mask 25 of the ion beam column 20 in order to efficiently form the deposition film.

Figure 22:
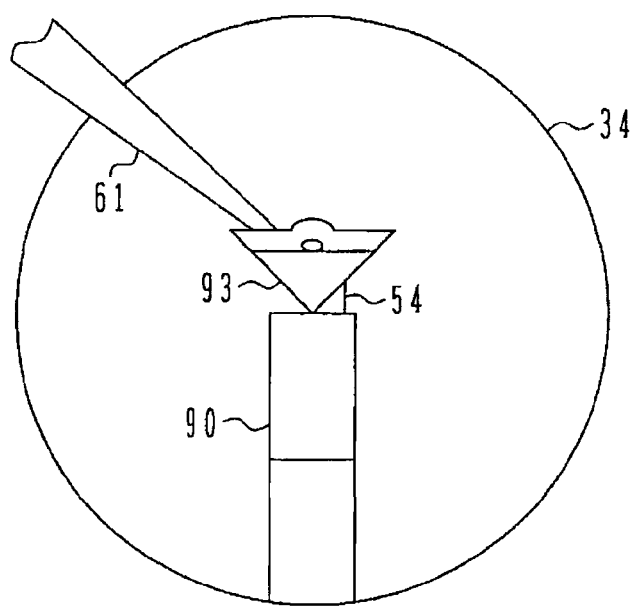
FIG. 22 shows the piece of sample being fixed onto a sample carrier of a cartridge.

In S210, as shown in FIG. 22, the probe 61 and the sample stage 33 are scanned to move the sample piece 93 over the sample carrier 90 retained on the cartridge 34. Then, while the deposition gas 52 is supplied to the point of contact between the piece of sample 93 and the sample carrier 90, the ion beam 22 is radiated to form a deposition film 54 by which the sample piece 93 and the sample carrier 90 are bonded to each other. With the piece of sample 93 thus mounted on the sample carrier 90, the probe 61 is separated from the piece of sample 93.

In S211, the cartridge 34 held on the sample holder 32 together with the sample 31 is delivered into the sample exchange chamber 35, where the cartridge is discharged by the cartridge transfer robot 37 into the cartridge case 39, thereby ending the procedure.

Figure 23:
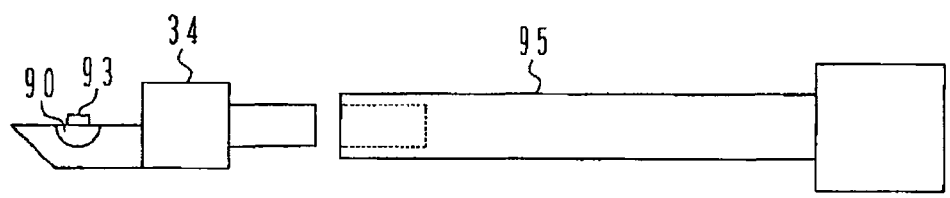
FIG. 23 shows an example of a cartridge and a sample holder.

The discharged cartridge 34 can be attached to the tip of a sample holder 95 (see FIG. 23) that can be inserted into the side entry stage of a high resolution analytical system such as a TEM or an STEM. Thus, a fine particle that cannot be sufficiently observed by the SEM or SIM can be observed in an image in detail provided by an electron microscope such as TEM or STEM having a higher resolution.

Figure 24:
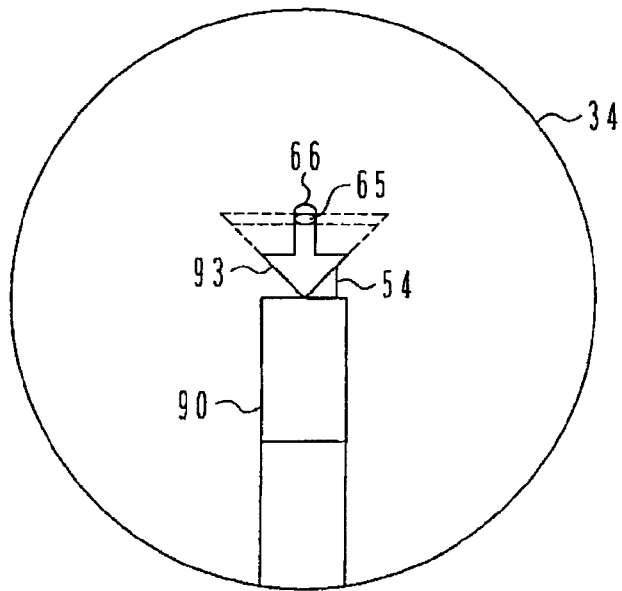
FIG. 24 shows the piece of sample that has been formed as a thin film.

The sample holder 95 can be inserted into the side entry stage of the ion beam processing system, so that it can be additionally processed with a narrowed ion beam from the Ga ion source. The piece of sample 93 extracted from the sample 31 is contaminated by the Ga ion beam irradiation; this, however, does not pose a problem as the sample piece is not returned to the line. As shown in FIG. 24, the piece of sample 93 in the form of a thin-film can be analyzed in detail using a high resolution analytical system, such as a TEM or an STEM. The thin-film piece of sample 93 enables a reduction in background noise during EDX analysis, so that an accurate analysis can be performed. It is also possible to form the piece of sample 93 into a thin-film by FIB processing in advance using the semiconductor inspection system of the present example.

Thus, in the present example too, the same effects as those of the foregoing first example can be obtained. When it is necessary to observe the particle with an TEM or STEM having a higher resolution than the SEM, it becomes possible to observe and analyze the particle in greater detail by selecting the operations of the present example.

Example 3

Figure 25:
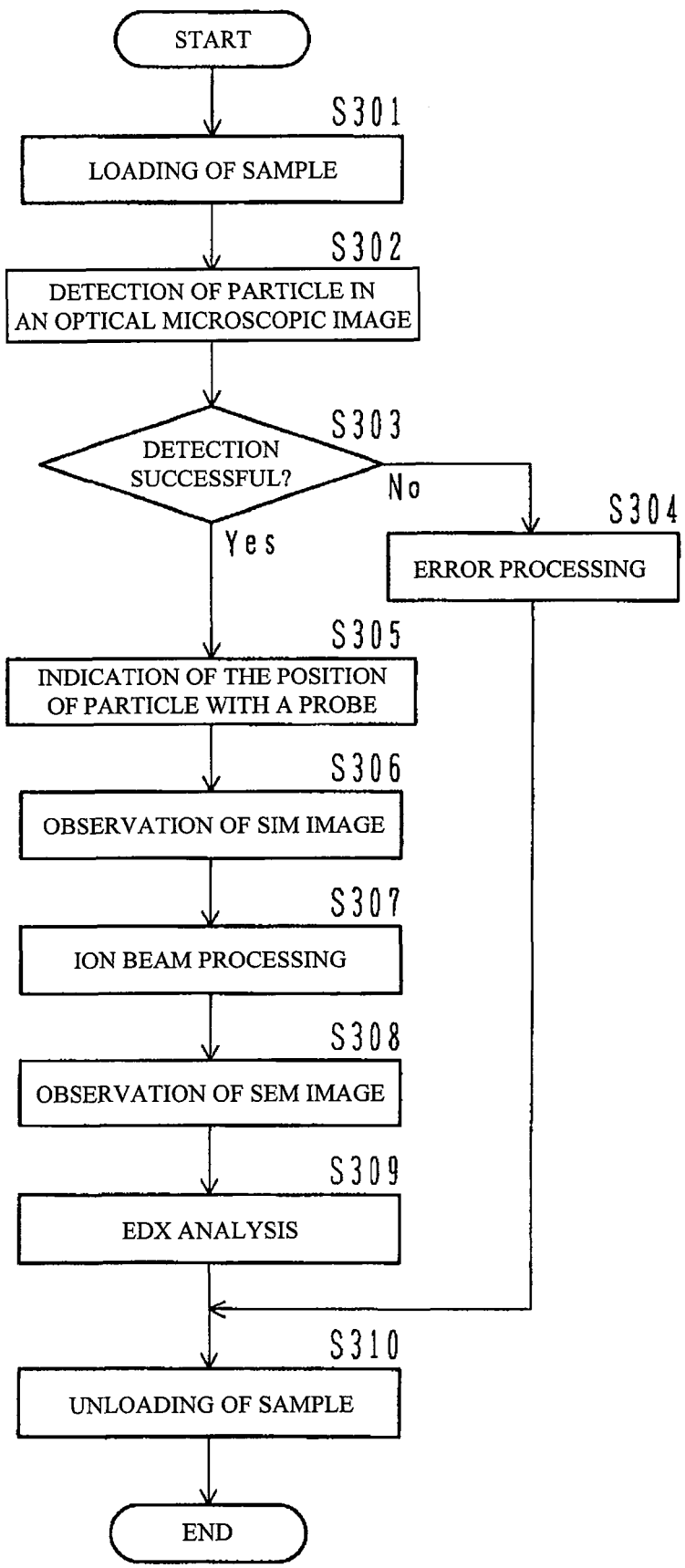
FIG. 25 shows a flowchart of a third example of the procedure for analyzing (reviewing) a defect portion in a sample that has been detected with the separate optical inspection system, using the semiconductor inspection system of the present embodiment.

FIG. 25 shows a flowchart of a third example of the procedure for analyzing (reviewing) the defect portion of the sample detected by the separate optical inspection system, using the semiconductor inspection system of the present embodiment The present example also involves a method of analysis suitable for the accurate analysis of a particle that exists in the film and that cannot be observed with an SEM image or SIM image sufficiently, using an electron microscope image with higher resolution. The third example is characterized by the manner of use of the probe 61, in comparison with the second example.

S301 to S304 are the same as S101 to S104 of the first example. If the detection of a defective site by the optical microscopic image is successful and the determination in S303 is satisfied, the procedure moves to S305.

Figure 26:
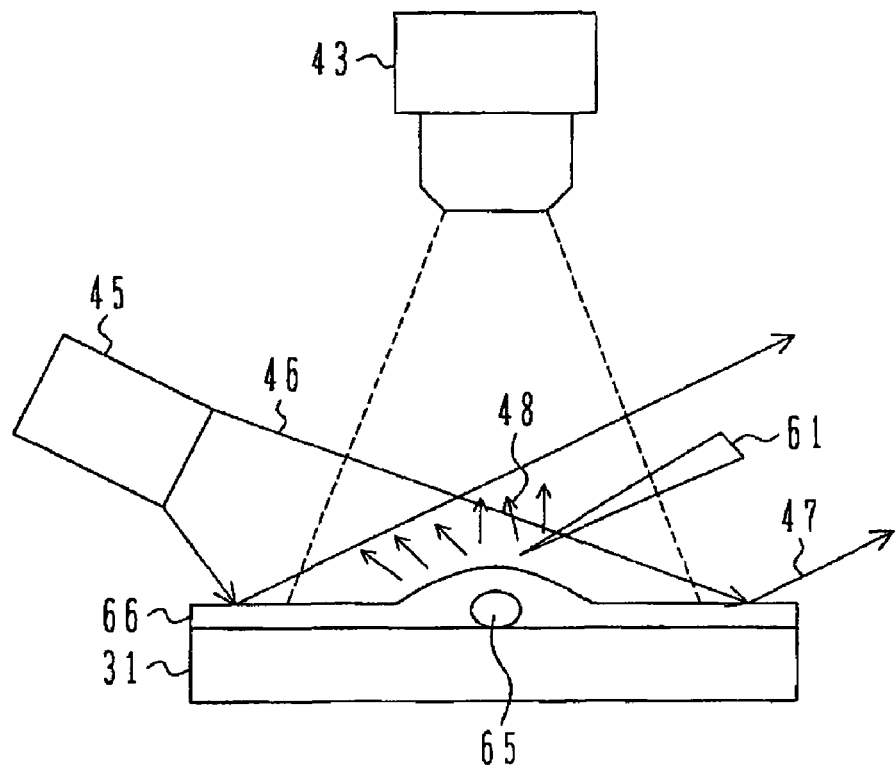
FIG. 26 shows a particle being detected using a dark field optical microscopic image.

FIG. 26 shows a structure for the detection of the particle 65 that exists in the film using the dark field light source 44 and the optical microscope 43.

Figure 27:
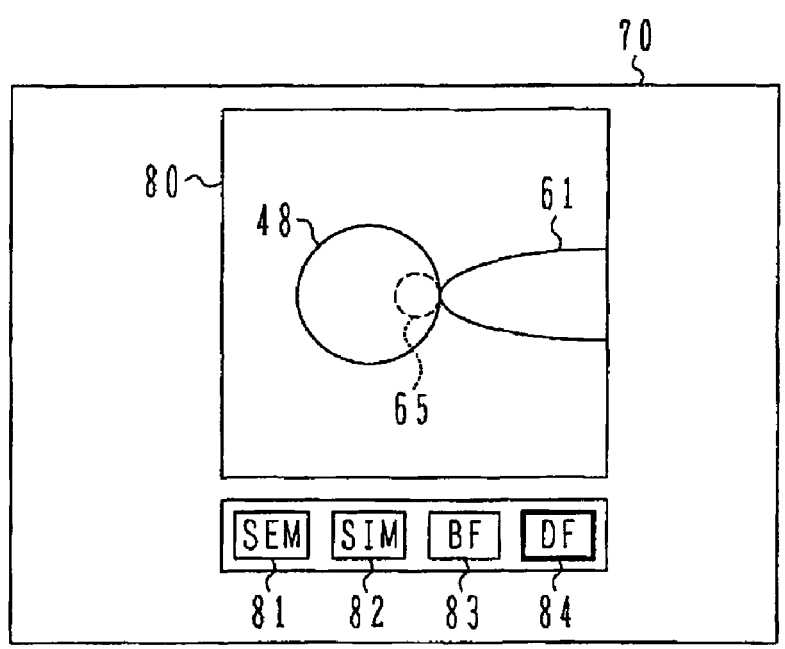
FIG. 27 shows a dark field optical microscopic image on which the probe has been transported near the particle.

In S305, the film 66 that is raised by the particle 65, as shown in FIG. 26, is irradiated with the illuminating light 46 from the dark field light source 45. The scattered light 48 produced is then observed with the optical microscope 43 so as to obtain a dark field optical microscopic image of the particle 65. The probe 61 is equipped with a mechanism for moving the ion beam irradiated position and its peripheral portions in at least the ion beam column 20 within the view field of the optical microscope 43. The probe 61 is transported near the particle 65 to support the particle 65 with the tip of the probe 61. At this time, by operating a DF button 84 in the display device 70, a dark field optical microscopic image can be displayed in the display area 80 of the display device 70, as shown in FIG. 27, showing the particle 65 being supported by the tip of the probe 61.

Figure 28:
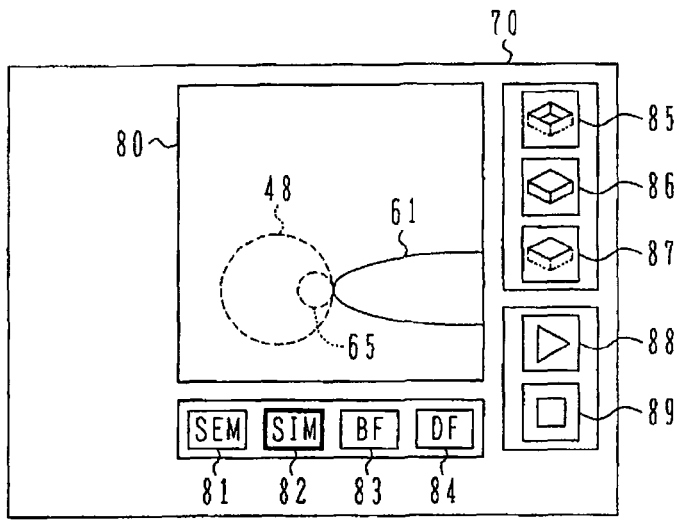
FIG. 28 shows an SIM image on display near the particle with reference to the probe as an indicator.
Figure 29:
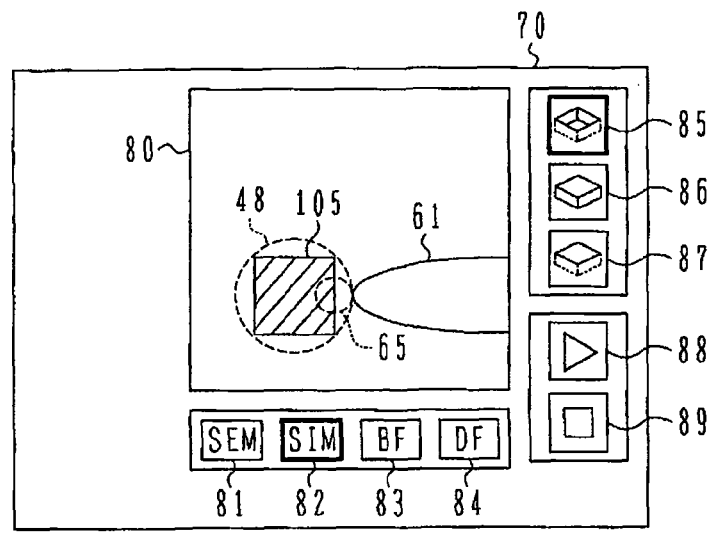
FIG. 29 shows an SIM image on which the processing position has been determined with reference to the probe as an indicator.

In S306, as shown in FIG. 28, an SIM button 82 of the display device 70 is operated to display an SIM image in the image display area 80, so that an SIM image in a region near where the dark field optical microscopic image has been observed using the ion beam column 20 is displayed in the display area 80. In the SIM image, no particle that exists in a film having a gradual surface can be observed. Therefore, as shown, only the probe 61 can be observed in the SIM image. At this time, since the field of view of the dark field optical microscopic image and that of the SIM image are not completely aligned to each other, the probe 61 is displayed at a position displaced from the dark field optical microscopic image. Therefore, as shown in FIG. 29, the position of the particle in the film is inferred on the SIM image with reference to the position of the displayed probe 61 and on the basis of the positional relationship between the probe 61 and the particle confirmed on the dark field optical microscopic image, and then a processed region 105 is designated.

Figure 30:
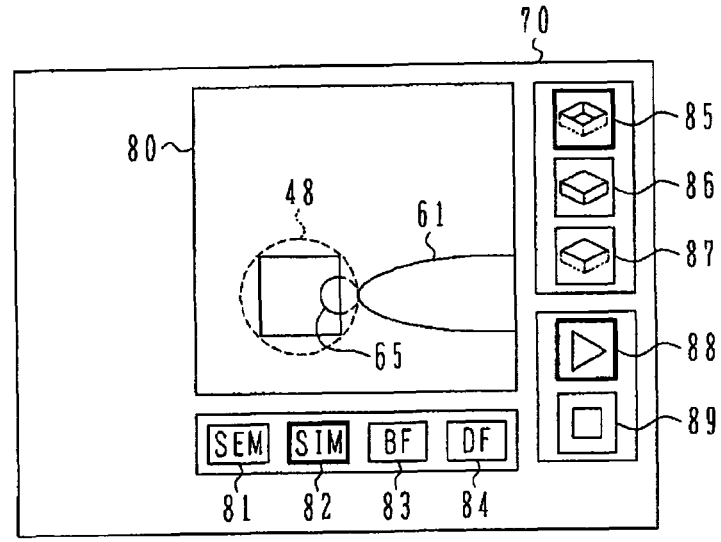
FIG. 30 shows an SIM image on which the state of processing with the processing ion beam is being monitored.

The procedure then moves onto S307 where the processed region 105 is irradiated with the ion beam, whereby the film 66 is processed as shown in FIG. 30 and the particle 65 that exists in the film is exposed to the surface. In the present example, the display device 70 is provided with buttons 85 to 89 for designating the shape of a processed opening to be formed in the sample or the shape of the ion beam, for example. Thus, the target shape of the processed opening or the ion beam can be designated by a combination of the individual buttons depending on the size or shape of the processed region 105 that has been set, in view of the shapes displayed in each of the buttons 85 to 89. In this way, the operation of FIB processing is facilitated.

Thereafter, the SEM button 81 on the display device 70 is operated to cause the display in the image display area 80 to be switched to an SEM image. After the particle 65 exposed by means of the electron beam column 10 is observed in the SEM image (S308) and subjected to EDX analysis (S309), the sample is unloaded as in S110 of the first example, thereby completing the analysis procedure of the present example.

In the present example too, the particle that exists in the film can be detected with the optical microscope 43, so that the same effects as those of the first example can be obtained. Furthermore, in the present example, since the probe 61 is used as an indicator of the processed site, the ion beam irradiation position can be easily inferred on the basis of the positional relationship with the image of the probe 61, regardless of the displacement in the field of view between the optical microscopic image and the SIM image. Thus, even in the absence of the function to display an optical microscopic image simultaneously with an SIM image or an SEM image on the display device, the film can be reliably removed while monitoring the SIM image.

In the present example, the probe 61 was moved to the indicator position near the particle on the dark field optical microscopic image. Due to the irradiation angle of the illuminating light, the target appears larger than it actually is on the dark field optical microscopic image. Therefore, it is preferable to operate the probe 61 while monitoring the dark field optical microscopic image from the viewpoint of precisely moving the probe 61. However, this operation can also be carried out on the bright field optical microscopic image. In the case of the dark field optical microscopic image, depending on the condition of the sample surface, it is difficult in some cases to detect scattered light and obtain a clear image. In such a case, the probe 61 can be operated while monitoring the positional relationship between the probe 61 and the particle on the bright field optical microscopic image.

Figure 31:
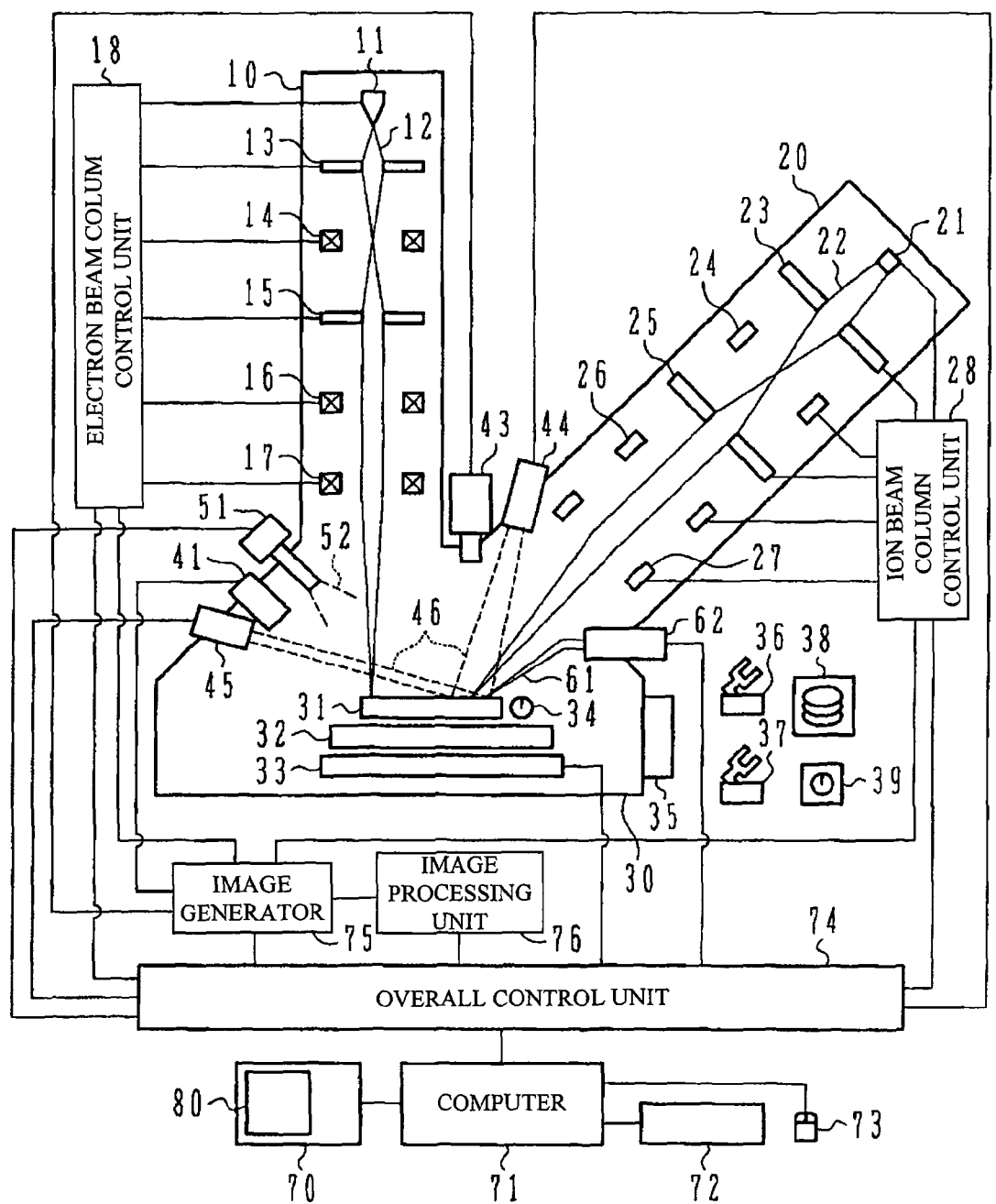
FIG. 31 schematically shows the overall structure of another embodiment of the semiconductor inspection system of the invention.

FIG. 31 shows an overall structure of another embodiment of the semiconductor inspection system of the invention. In FIG. 31, parts similar to or parts that perform similar functions to those of the already described drawings are referenced with similar numerals and their descriptions are omitted.

As shown in FIG. 31, in the semiconductor inspection system of the present example, the electron beam column 10 for the irradiation of the electron beam 12 is mounted vertically. In this case, the optical microscope 43 for capturing the field of view of the ion beam column 20 is disposed above the field of view of the ion beam column 20, which is used for the irradiation of the ion beam 22. As a result, it is physically difficult to dispose the electron beam column 10 and the ion beam column 20 such that they have the same point in their fields of view, resulting in different view fields for the SEM image and the SIM image.

Specifically, in the present embodiment, the electron beam column 10 and the ion beam column 20 are disposed such that the beam target position of the electron beam and that of the ion beam are spaced apart from each other. For this reason, the optical microscope 43 is provided with a transfer mechanism so as to allow the optical microscope 43 to be movable between the position at which the beam target position of the electron beam column can be captured in the view field and the position at which the beam target position of the ion beam column can be captured in the view field. Thus, the bright field light source 44 and the dark field light source 45 are also made movable with the optical microscope 43, or the irradiated region of the illuminating light is made deflectable depending on the view field of the optical microscope 43. Alternatively, the optical microscope 43 may be structured such that its direction of observation can be changed. Further alternatively, an optical microscope for the observation of the ion beam target position and an optical microscope for electron beam observation may be separately provided.

In the structure of the present embodiment too, it is possible to analyze the particle that exists within a film by installing the optical microscope 43 in alignment with the view field of the SIM image, which is associated with the irradiation of a projection ion beam. Thus, the same analysis procedure as those of the foregoing examples can be performed. Alternatively, the optical microscope 43 may be provided with a transfer mechanism for moving the view field, so that the view field of the SEM image and the view field of the SIM image can be individually observed.

While the embodiments of the invention have been described above, the invention is not limited by any of the foregoing embodiments, and it should be obvious to one skilled in the art that various changes can be made within the scope of the claims.

For example, while in the foregoing, the X-ray detector 42 was described as being provided in the system, the essential purpose is to precisely capture a particle that is difficult to observe with an electron microscope image or an ion microscope image, by means of the concurrently provided optical microscope 43, thereby allowing a quick acquisition of an electron microscope image or an ion microscope image, so that the procedure can move onto the FIB processing or the EDX analysis quickly. Thus, the X-ray detector needs not be provided but rather it may be added later. It is also possible to analyze the processed sample on a separate EDX analysis apparatus.

While in the foregoing the bright field light source 44 and the dark field light source 45 have been described as being separately provided, they may be combined into a common light source; in this case, a light source moving mechanism is employed to provide the functions of the bright field light source and the dark field light source. Furthermore, while the image generator 75 generated both an electron microscope image and an optical microscope image, a separate image generators may be provided. Instead of, or in addition to, the secondary electron detector 41, a transmission electron detector for detecting transmission electrons that transmitted the sample may be provided as a sample signal detector so as to allow TEM or STEM observation with the electron beam column 10.

Further, while in the foregoing, examples were described in which a sample inspected by a separate optical inspection system was analyzed in detail with the semiconductor inspection system of the invention, there may be cases where a sample that has not been inspected by the separate optical inspection system is inspected with the optical microscope 43 implemented in the present semiconductor inspection system, and, upon detection of a defect, the particle is subjected to observation or an ultimate analysis in detail through the same procedure as each of the above-described flows. Further, while the examples involved the detailed analysis of the particle in (or under) the film in detail, it goes without saying that the semiconductor inspection system of the invention can be applied for the observation of a defective site on the film surface.

The semiconductor inspection system of the invention can be used not only for the observation/analysis of a defect in semiconductor devices such as microprocessors or memories, but it can also be used as a charged particle beam system for the inspection/analysis of a defective site in a target object other than semiconductors, such as liquid crystal, hard discs, and other precision components, products, or semifinished products.

What is claimed is:

1. A charged particle beam system comprising:
   a sample stage movable with a wafer mounted thereon;
   a sample chamber enclosing the sample stage;
   an electron beam column connected to the sample chamber and having an electron source and an electron beam optical system for focusing an electron beam drawn from the electron source and scanning and irradiating the wafer with the electron beam;
   an ion beam column connected to the sample chamber and having a nonmetal gas ion source, which generates a nonmetal gas so that liquid metal ion source contamination of the wafer does not occur, and an ion beam optical system for irradiating the wafer with an ion beam drawn from the gas ion source;
   a sample signal detector for detecting a sample signal for generating a microscope image that is obtained by irradiating the wafer with the electron beam from the electron beam column or the ion beam from the ion beam column;
   an image generator for generating an electron microscope image or an ion microscope image by acquiring a detection signal from the sample signal detector;
   an optical microscope disposed in the sample chamber such that an ion beam target position of the ion beam column is within the view field of the optical microscope;
   an image generator for generating an optical microscope image of the wafer by acquiring condition data from the optical microscope; and
   a probe movable within the view field of the optical microscope at or around an ion beam target position of the ion beam column for holding a piece extracted from the wafer by ion beam irradiation;
   wherein the electron beam column and the ion beam column are disposed such that the beam target position of the electron beam and that of the ion beam are spaced apart from each other.

2. The charged particle beam system according to claim 1, further comprising a bright field light source for irradiating the wafer with illuminating light for photographing a bright field image with the optical microscope.

3. The charged particle beam system according to claim 1, further comprising a dark field light source for irradiating the wafer with illuminating light for photographing a dark field image with the optical microscope.

4. The charged particle beam system according to claim 2, wherein the bright field light source is mounted movably such that the angle of irradiation of illuminating light can be changed, the bright field light source thus also functioning as a dark field light source for irradiating the wafer with illuminating light for photographing a bright field image with the optical microscope.

5. The charged particle beam system according to claim 1, wherein the ion beam column comprises a mask having a plurality of differently shaped mask openings, wherein the shape of the ion beam can be changed by moving the mask so as to switch the mask sharp through which the ion beam is passed, or withdrawing the mask from the ion beam so as to prevent the mask from interfering the ion beam.

6. The charged particle beam system according to claim 1, further comprising a deposition gas source for supplying deposition gas to the ion beam irradiated position and filling a remaining processed opening in the wafer after extracting the piece from the wafer.

7. The charged particle beam system according to claim 1, further comprising a transfer mechanism for moving the optical microscope between a position at which the beam target position of the electron beam column can be captured and a position at which the beam target position of the ion beam column can be captured, within the view field of the optical microscope.

8. The charged particle beam system according to claim 1, wherein the sample signal detector comprises a secondary electron detector that detects secondary electrons generated by the wafer upon irradiation with the electron beam from the electron beam column.

9. The charged particle beam system according to claim 1, wherein the sample signal detector comprises a transmission electron detector for detecting transmission electrons upon transmission of the electron beam from the electron beam column through the wafer.

10. The charged particle beam system according to claim 1, further comprising an X-ray detector for detecting characteristic X-ray emitted by the wafer upon irradiation with the electron beam from the electron beam column.

11. A sample processing method using the charged particle beam system according to claim 1, wherein, after the detection of a particle attached to the wafer with the optical microscope, if the particle cannot be observed with an electron microscope image or an ion microscope image, the position of the particle is confirmed with an optical microscope image and the film that covers the particle is partially removed with the ion beam from the ion beam column, and then a microscope image is acquired on the basis of a sample signal that is obtained upon irradiation of the exposed particle with the electron beam or the ion beam.

12. The sample processing method according to claim 11, wherein the exposed particle is irradiated with the electron beam from the electron beam column, and then characteristic X-ray emitted by the particle is detected with an X-ray detector and used for ultimate analysis of the particle.

13. A sample processing method using the charged particle beam system according to claim 5, wherein, after the detection of a particle attached to the wafer with the optical microscope, if the particle cannot be observed with an electron microscope image or an ion microscope image, the position of the particle is confirmed with an optical microscope image, and then a piece of wafer containing the particle is cut out of the wafer using an ion beam whose shape has been changed by operating the mask.

14. A sample processing method using the charged particle beam system according to claim 6, wherein the ion beam column comprises a mask having a plurality of differently shaped mask openings, wherein, after the detection of a particle attached to the wafer with the optical microscope, if the particle cannot be observed with an electron microscope image or an ion microscope image, the position of the particle is confirmed with an optical microscope image, a piece of wafer containing the particle is cut out of the wafer using an ion beam whose shape has been changed by operating the mask, and then the piece of wafer that has been cut out is attached to the probe for extraction.

15. A sample processing method using the charged particle beam system according to claim 6, wherein, after the detection of a particle attached to the wafer with the optical microscope, if the particle cannot be observed with an electron microscope image or an ion microscope image, the probe is transported near the particle while monitoring an optical microscope image so as to indicate the position of the particle with the probe, the position of the particle is inferred in an SIM image with reference to the probe as an indicator, and then the thus determined processing position is processed with the ion beam.

16. A semiconductor inspection system comprising:
  a sample stage movable with a semiconductor wafer mounted thereon;
  a sample chamber enclosing the sample stage;
  an electron beam column connected to the sample chamber and having an electron source and an electron beam optical system for focusing an electron beam drawn from the electron source and scanning and irradiating the semiconductor wafer with the electron beam;
  an ion beam column connected to the sample chamber and having a nonmetal gas ion source, which generates a nonmetal gas so that liquid metal ion source contamination of the wafer does not occur, and an ion beam optical system for irradiating the semiconductor wafer with an ion beam drawn from the gas ion source;
  a sample signal detector for detecting a sample signal for generating a microscope image that is obtained by irradiating the semiconductor wafer with the electron beam from the electron beam column or the ion beam from the ion beam column;
  an image generator for generating an electron microscope image or an ion microscope image by acquiring a detection signal from the sample signal detector;
  an optical microscope disposed in the sample chamber such that an ion beam target position of the ion beam column is within the view field of the optical microscope;
  an image generator for generating an optical microscope image of the semiconductor wafer by acquiring condition data from the optical microscope; and
  a probe movable within the view field of the optical microscope at or around an ion beam target position of the ion beam column for holding a piece extracted from the wafer by ion beam irradiation;
  wherein the electron beam column and the ion beam column are disposed such that the beam target position of the electron beam and that of the ion beam are spaced apart from each other.

* * * * *